(12) United States Patent
Chu et al.

(10) Patent No.: US 8,012,080 B2
(45) Date of Patent: Sep. 6, 2011

(54) SYSTEMS AND METHODS FOR SLING DELIVERY AND PLACEMENT

(75) Inventors: Michael S. H. Chu, Brookline, MA (US); Brian Charles MacLean, Waltham, MA (US); Kenneth J. Daignault, Holden, MA (US); Michael G. McGrath, Hudson, MA (US)

(73) Assignee: Boston Scientific Scimed, Inc., Boston, MA (US)

( * ) Notice: Subject to any disclaimer, the term of this patent is extended or adjusted under 35 U.S.C. 154(b) by 1495 days.

(21) Appl. No.: 10/832,653

(22) Filed: Apr. 26, 2004

(65) Prior Publication Data

US 2004/0225181 A1 Nov. 11, 2004

Related U.S. Application Data

(60) Provisional application No. 60/465,722, filed on Apr. 25, 2003.

(51) Int. Cl.
*A61F 2/02* (2006.01)
(52) U.S. Cl. .......................................... 600/30

(58) Field of Classification Search ............... 600/29–31, 600/37; 606/144, 151, 167; 128/885, 897, 128/898
See application file for complete search history.

(56) References Cited

U.S. PATENT DOCUMENTS

| | | | |
|---|---|---|---|
| 5,362,294 A | 11/1994 | Seitzinger | |
| 5,439,467 A | 8/1995 | Benderev et al. | |
| 6,110,101 A | 8/2000 | Tihon et al. | |
| 6,478,727 B2 * | 11/2002 | Scetbon | 600/30 |
| 6,685,629 B2 * | 2/2004 | Therin | 600/37 |
| 6,752,814 B2 * | 6/2004 | Gellman et al. | 606/148 |
| 2001/0049467 A1 * | 12/2001 | Lehe et al. | 600/30 |
| 2002/0091373 A1 | 7/2002 | Berger | |
| 2003/0009181 A1 | 1/2003 | Gellman et al. | |
| 2003/0045774 A1 | 3/2003 | Staskin et al. | |

FOREIGN PATENT DOCUMENTS

| | | |
|---|---|---|
| EP | 1093758 | 4/2001 |
| WO | WO-92/07517 | 5/1992 |
| WO | WO-97/47246 | 12/1997 |
| WO | WO-98/35616 | 8/1998 |

\* cited by examiner

*Primary Examiner* — Charles A Marmor, II
*Assistant Examiner* — Christine D Hopkins
(74) *Attorney, Agent, or Firm* — Bingham McCutchen LLP

(57) ABSTRACT

Devices and methods for delivering and placing a surgical sling without resorting to an abdominal incision are disclosed.

26 Claims, 17 Drawing Sheets

SYSTEMS AND METHODS FOR SLING DELIVERY AND PLACEMENT

RELATED APPLICATIONS

This application claims priority to U.S. Provisional Application No. 60/465,722, filed Apr. 25, 2003, the specification of which is incorporated herein by reference in its entirety.

BACKGROUND OF THE INVENTION

Stress urinary incontinence (SUI) affects primarily women, but also men, and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow.

A popular treatment of SUI uses a surgical sling placed under the bladder neck or the mid-urethra to provide a urethral platform. Placement of the sling limits the endopelvis fascia drop while providing compression to the urethral sphincter to improve coaptation. The mid-urethral sling is traditionally affixed using a bone anchoring method. Recent advances in surgical techniques have demonstrated the effectiveness of anchorless approaches toward mid-urethra sling stabilization. However, these anchorless techniques typically require incisions in addition to those made in the vaginal wall. By way of example, some procedures require abdominal incisions, while others require ishiopubic incisions.

Accordingly, there is a need for an improved approach to sling placement that simplifies the procedure and reduces trauma to the patient.

SUMMARY OF THE INVENTION

The systems and methods described herein are generally directed to the delivery and application of an implant to an anatomical site in a patient. More particularly, in one embodiment, the systems and methods of the invention are suitable for sub-urethral implantation of an implantable sling into the periurethral tissue, without the need for abdominal or ishiopubic incisions. According to a further embodiment, the invention avoids any need for bone anchors to anchor the sling in place.

In one aspect, the invention provides a system for treating urinary incontinence in a patient, including: a first elongated delivery device having a proximal end and a distal end, a first aperture located near the distal end, a second aperture located near the proximal end, and a lumen extending between the first and second apertures; and a sling assembly including a sling at least partially enclosed by a sleeve, the sling assembly having a first end threaded through into the first aperture, through the lumen and out the second aperture of the first elongated delivery device.

According to one embodiment, the sleeve is longer than the sling and a portion of the sleeve not enclosing the sling threads into the first aperture, through the lumen and out the second aperture. According to one configuration, the first elongated delivery device includes a frustoconical tip as its distal end, the conical tip being sufficiently pointed to pierce and tunnel through tissue. In another configuration, the tip at the distal end of the delivery device is rounded. According to an alternative configuration, the first aperture is located at a termination of the distal end of the first elongated delivery device. In another configuration, the first aperture is located in a side wall near the distal end of the first elongated delivery device. In a similar fashion the second aperture may be located at a termination of the proximal end of the first elongated delivery device, or alternatively, in a side wall near the proximal end of the first elongated delivery device.

The sling assembly, preferably, includes a tabbed spacer located along a bottom surface of the sleeve, and engages a portion of the bottom surface of the sleeve to inhibit the sleeve from sliding off the sling, without first cutting through the tabbed spacer. In one embodiment, the tabbed spacer engages a looped portion of the bottom surface of the sleeve. In an alternative embodiment, the tabbed spacer engages sleeve tails of the bottom surface of the sleeve.

In some embodiments, only the sleeve end extends into the first elongated delivery device. However, in other embodiments, the sling has a first end that extends into the lumen of the first elongated delivery device.

According to another feature, the system includes an operator actuatable cutting device located in the lumen for cutting off a portion of at least one of the sling and the sleeve. In one configuration, the actuator operatively connects to the cutter and extends from the cutter through the lumen and out the second aperture, the cutter being actuated by pushing the actuator in a distal direction.

According to one configuration, the first elongated delivery device includes a handle located near its proximal end. In a related configuration, the first elongated delivery device includes a shaft having a first straight portion extending distally along an axis from a distal end of the handle and a curved portion first curving away from the axis and then curving back toward the axis. In some embodiments, the curved portion does not extend to the axis subsequent to curving back toward the axis. However, in other embodiments, the curved portion extends to or crosses the axis subsequent to curving back toward the axis.

In some embodiments, the system includes two elongated delivery devices, sometimes referred to below as delivery legs. According to one such embodiment, the system includes, a second elongated delivery device having a proximal end and a distal end, a first aperture located near the distal end, a second aperture located near the proximal end, and a lumen extending between the first and second apertures, and the sling assembly has a second end threaded through into the first aperture, through the lumen and out the second aperture of the second elongated delivery device.

In one aspect, the system includes a handle having proximal and distal ends, wherein the proximal ends of the first and second elongated delivery devices intersect with the distal end of the handle to form a substantially "Y"-shaped delivery system configuration. In one embodiment, the proximal ends of the first and second elongated delivery devices attach to the distal end of the handle. In another embodiment, the proximal ends of the first and second elongated delivery devices are formed integrally with the distal end of the handle. In a further embodiment, the first and second elongated delivery devices are sufficiently flexible for an operator to squeeze them together during a sling implantation procedure. According to one feature, the first and second elongated delivery devices are sufficiently resilient to substantially return to an original shape in response to the operator removing a squeezing force.

In a related feature, the handle is sufficiently flexible for an operator to squeeze the first and second elongated delivery devices together.

According to another aspect, the invention does not employ a sleeve to partially enclose the sling. In this aspect, the system includes; a first elongated delivery device having a proximal end and a distal end, a first aperture located near the distal end, a second aperture located near the proximal end, and a lumen extending between the first and second apertures; and a sling assembly including a sling having first and second ends, at least the first end being operatively associated with the distal end of the first elongated delivery device. According to one embodiment, the first end attaches to a suture, and the suture threads through the first aperture located near the distal end of the delivery device. In a further embodiment, the suture passes through the first aperture near the distal end through the lumen and out the second aperture near the proximal end.

According to a related embodiment, the system includes an engaging device attached to an end of the suture, and a receptacle near the distal end of the first delivery device for engaging with the engaging device of the sling. In operation, the engaging device is engaged with a distal end of a delivery device and inserted by the distal end of the delivery device through an incision in a vaginal wall of a patient along a first side of the patient's urethra to position the first end of the sling in periurethral tissue on the first side of the patient's urethra, without making any abdominal or ishiopubic incisions. Then the engaging device, along with the first end of the sling assembly, is disengaged from the distal end of the delivery device which is withdrawn.

In another aspect, the invention provides a method for implanting a sling under a urethra in a body of a patient, the method comprising: threading an end of a sleeve at least partially enclosing a sling through into an aperture near a distal end of delivery device, through a lumen extending along at least a portion of a length of the delivery device, and out an aperture near a distal end of the delivery device; inserting the distal end of the delivery device through an incision in a vaginal wall along a first side of the urethra; sliding the sleeve off the sling through the lumen of the delivery device out of the body of the patient; and leaving the sling in the body of the patient to support the urethra. According to one embodiment, the method includes positioning an end of the sling in front of the pubic bone. In an alternative embodiment, the method includes positioning an end of the sling behind the pubic bone. In another embodiment, the method includes positioning an end of the sling near the pubic bone. In other embodiments, the method includes positioning an end of the sling near or through an obturator foramen.

Further features and advantages of the invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

ILLUSTRATIVE DESCRIPTION

In general, the invention is directed to systems and methods for the treatment of urinary incontinence. In one illustrative embodiment, the invention provides simplified systems and methods for delivering and placing a medical implant to an anatomical site of a patient, with reduced trauma to the patient. In a preferred embodiment, the medical implant is a sling for treating urinary incontinence and it is delivered to the periurethral tissues of either a female or male patient. According to one advantage, the systems and methods of the invention avoid the need for any abdominal incisions during sling placement. According to a further advantage, the invention also avoids the need for any ishiopubic incisions during sling placement. According to a further feature, the invention also avoids the need for any bone anchors to anchor the sling in place.

Figure 1:
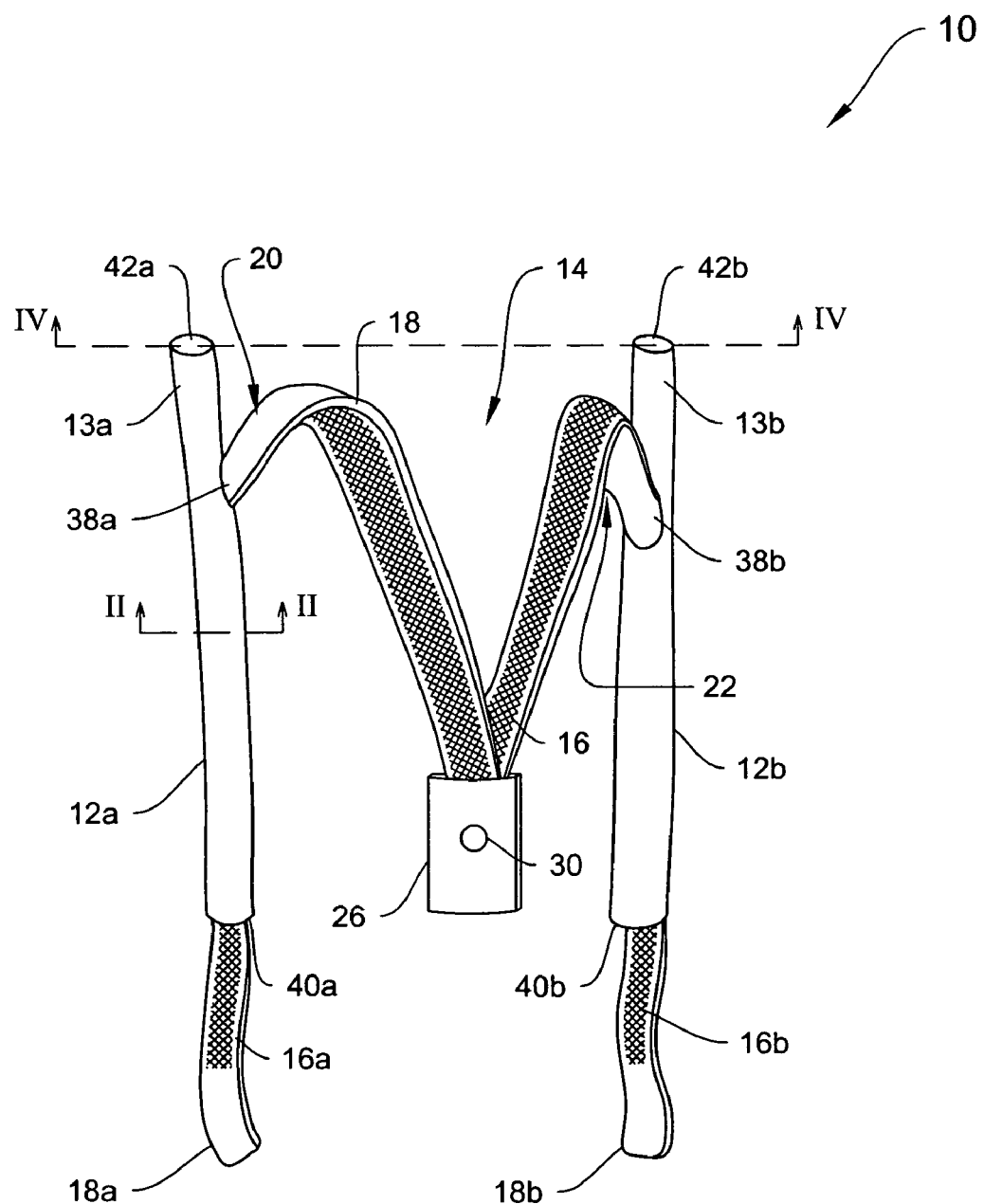
FIG. 1 depicts a sling delivery system for delivering a sling to an anatomical site of a patient according to an illustrative embodiment of the invention.
Figure 3:
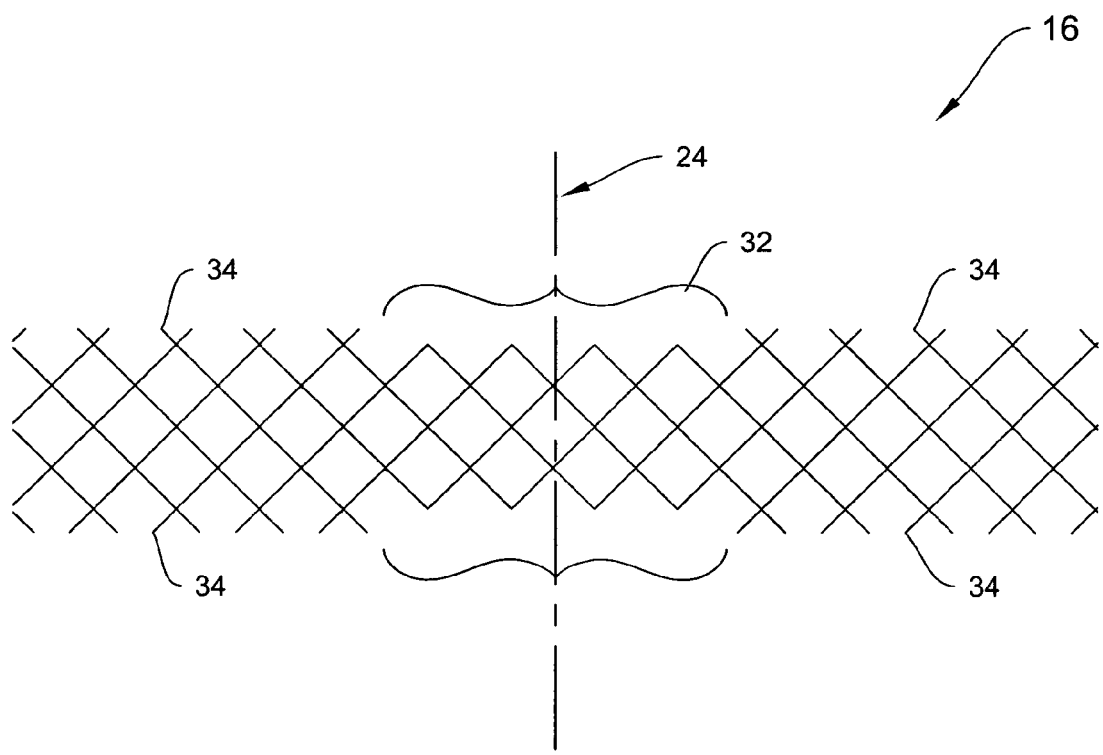
FIG. 3 depicts a mesh sling illustrative of a type that may be employed with the sling delivery system of FIG. 1.
Figure 4:
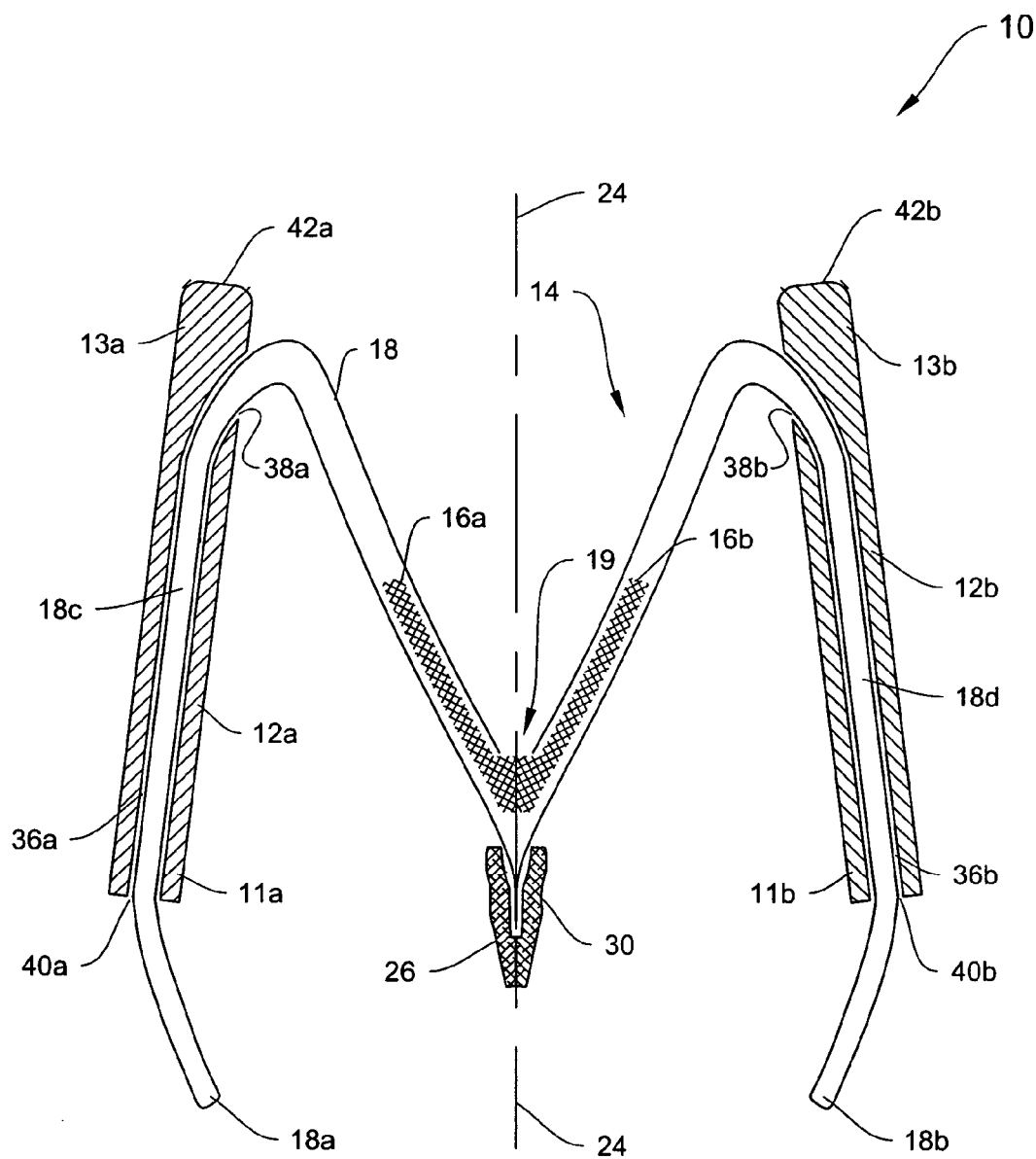
FIG. 4 is a cross-sectional view, along the line IV-IV of the illustrative sling delivery system of FIG. 1.

FIG. 1 shows a sling delivery system 10 according to an illustrative embodiment of the invention. The sling delivery system 10 includes delivery devices 12a and 12b and a sling assembly 14. Referring also to FIGS. 3 and 5C, the sling assembly 14 includes a sling 16 and a sleeve 18. The sleeve 18 is formed from a flexible material, such as a flexible polymer plastic, and partially encloses the sling 16. The sleeve 18 includes an upper surface 20 and a lower surface 22. Referring also to FIG. 4, an opening 19, located at a midpoint 24 of the upper surface 20 of the sleeve 18, exposes the entire width of the sling 16.

Referring also to FIG. 3, in some illustrative embodiments the sling 16 has a length of about 10 to about 15 cm (about 4-6 inches) and a width of about 1 to about 3 cm, though the length and width of the sling 16 can be adapted to the body part of the patient that requires support. By way of example, in some embodiments the sling 16 is about 45 cm in length. The sling 16 may be rectangular, as illustrated in FIG. 3, or have another suitable shape. The sling 16 may have a uniform thickness over the entire length and/or width of sling 16. Alternatively, the thickness can be suitably varied at one or more locations. The thickness of the sling 16 material may range from about 0.02 to about 0.10 cm. In one embodiment, the sling 16 is a strip of mesh with any of a number and/or configurations of knits, weaves, or braids.

The sling 16 may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials can include polyglycolic acid, polylactic acid, and other suitable absorbable synthetic materials. Alternatively, the material for the sling 16 may be derived from mammalian tissue(s) or a combination of mammalian tissue(s) and synthetic material(s). The sling material may be fabricated from one or more yarns, which yarns may be made from one or more materials. The sling 16 may incorporate or be coated with one or more agents to provide a therapeutic effect, for example, to reduce discomfort, to reduce the chance of infection and/or to promote tissue growth.

Referring back to FIG. 1 and also to FIG. 3, in one embodiment, the edge regions of the sling 16 can be configured differently depending on their intended placement in the body of the patient. For example, a midsection 32 of the sling 16 is typically located where an anatomical site, such as a midurethral or bladder neck location in the periurethral tissue, needs to be supported. In one illustrative embodiment, the midsection 32 of the sling 16 has smooth or rounded edges, hereinafter also referred to as "non-tanged." According to a further illustrative embodiment, other sections of the sling 16 may include tangs (e.g., sharp projections or frayed edges) 34. The tangs 34 are generally useful for anchoring the sling 16 and encouraging tissue growth into the sling 16. Anchoring the sling 16 in this manner generally obviates the need for additional sutures to hold the sling 16 in place.

The tanged and non-tanged edges of sling 16 can be formed in a plurality of ways. For example, the sling 16 can be cut from a woven sheet, in which case the edges would be initially tanged along the entire length of the sling 16. One or more non-tanged sections may be formed by any process that smoothes, rounds or removes the sharp edges of the tangs 34. For example, the tangs 34 may be heat-smoothed by burning or melting the tangs 34. In one embodiment, the non-tanged section 32 has a length of about 1 to about 5 cm, preferably about 2 to about 2.5 cm, on either or both sides of the center line 24. Providing one or more non-tanged sections, which may be in close proximity to a sensitive anatomical site in the patient, can enhance the comfort level of the patient and reduce the potential for the edges of the tangs to erode or irritate the urethra.

Alternatively, the sling 16 can be produced from a woven tape having the approximate finished width of the sling 16. The smooth sides of the tape can then be trimmed off to produce the tanged sections 34.

In the illustrative embodiment, the sling 16 terminates at free ends 16a and 16b. According to the illustrative embodiment, the sling 16, including both free ends 16a and 16b, does not connect to the sleeve 18 or anything else. This feature enables a medical operator to pull on the ends 18a and 18b of the plastic sleeve 18 during placement of the sling 16, without risk of stretching, curling or otherwise deforming the sling 16. As shown in FIG. 1, in some embodiments, the sling 16 is long enough so that the sling ends 16a and 16b extend through the delivery devices 12a and 12b. However, as shown in FIG. 4, in a preferred embodiment, the sling 16 is sized so that its ends 16a and 16b do not extend into delivery devices 12a and 12b.

A tabbed spacer 26 is located at a midpoint 24 of the lower surface 22 of the sleeve 18, and encloses a looped portion 28 of the bottom surface 22 of the sleeve 18. In one embodiment, the tabbed spacer 26 has a color different from that of the sleeve 18 or of the sling 16 to allow ready identification during the sling placement procedure. The tabbed spacer 26 can be used during implantation as a visual aid to placement of the sling 16.

As discussed in detail below with respect to FIG. 5, according to one feature, the tabbed spacer 26 is formed as cylinder. The looped portion 28 of the bottom surface 22 of the sleeve is fitted into the cylinder, and the cylinder is then flattened over the looped portion 28 and affixed to the looped portion 28, for example, using heat bonding, or any other suitable bonding approach. The tabbed spacer 26 engages the looped portion 28 of the bottom surface 22 of the sleeve 18 and prohibits the sleeve 18 from sliding off, or otherwise being removed from, the sling 16 during sling placement. According to the illustrative embodiment, the tabbed spacer 26 is cut across the center aperture 30 to enable the sleeve 18 to be slid off the sling 16. According to one feature, the tabbed spacer 26 ensures that the sleeve 18 does not slide off the sling 16 simply by applying a pulling force, such as that applied to the sleeve ends 18a and 18b by a medical operator during sling placement. After the sling assembly 14 is positioned within the patient, a cut is made through the center aperture 30 of the tabbed spacer 26, and thus through the looped portion 28 of the bottom surface 22 of the sleeve 18. The sleeve 18 can then be slid off of the sling 18 and out of the body of the patient by pulling on the sleeve ends 18a and 18b. Although the bottom surface 22 is described here as being continuous, as discussed below with respect to FIG. 5, in various alternative embodiments, it may be divided, for example at its center 24, and inserted into the tabbed spacer 26 as two separated tails, rather than a continuous looped portion 28.

Figure 2:
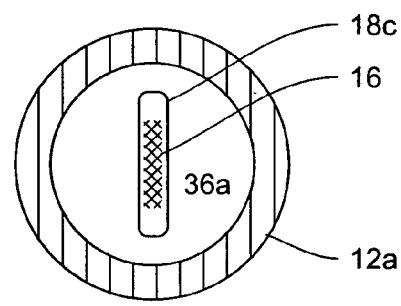
FIG. 2 is a cross-sectional view taken along the line II-II of the sling delivery system of FIG. 1.

FIG. 4 is a cross-sectional view of the sling delivery system 10, taken along the line IV-IV of FIG. 1. Referring to FIGS. 1 and 4, the two delivery devices 12a and 12b, preferably, have substantially identical structures. Referring to FIGS. 1 and 2, the illustrative delivery devices 12a and 12b are formed as tubes or cylinders that define lumens 36a and 36b, respectively. In one illustrative embodiment, the lumen 36a extends from a radial aperture 38a to a first end aperture 40a located at a proximal end 11a of the delivery device 12a. In some embodiments, the distal end 13a of the delivery device 12a is closed. However, in alternative embodiments, the lumen 36a also extends to a second end aperture 42a in the distal end 13a of the delivery device 12a. In a similar fashion, the lumen 36b extends from a radial aperture 38b to a first end aperture 40b at the proximal end 11b of the delivery device 12b, and the distal end 13b of the delivery device 12b is closed. As in the case of the delivery device 12a, the lumen 36b may also extends to a second end aperture 42b in the distal end 13b of the delivery device 12b. The delivery devices 12a and 12b may taper towards their respective distal ends 13a and 13b, and optionally, may come to a conical tip sufficient for dilation of and tunneling through tissue. Additionally, the delivery devices 12a and 12b may be straight, curved, or have a combination of straight and curved sections.

As shown in FIG. 4, when assembled, section 18c of the sleeve 18 threads into the radial aperture 38a through the lumen 36a and out the end aperture 40a of the delivery device 12a, while section 18d of the sleeve 18 threads into the radial aperture 38b through the lumen 36b and out the end aperture 40b of the of the delivery device 12b. As discussed below with respect to FIGS. 7A-7C, a medical operator may pull on the sleeve ends 18a and 18b extending from the delivery devices 12a and 12b, subsequent to cutting through the tabbed spacer 26, and thus cutting through the looped portion 28 of the bottom surface 22 of the sleeve 18, to slide the sleeve 18 off the sling 16 through the lumens 36a and 36b.

The delivery devices 12a and 12b can assume a variety of cross-sectional shapes. Referring to FIG. 2, the cross section of the delivery device 12a, taken along line II-II is oval in shape, and more preferably circular in shape. However, in alternative embodiments, any suitable cross-sectional shape may be employed. Additionally, cross-sections taken at various points along the length of the delivery device 12a may vary in size and/or shape. According to the illustrative embodiment, the delivery device 12b has a substantially identical cross-section to the delivery device 12a.

Preferably, the delivery devices 12a and 12b are made of biocompatible materials, which can include, for example, polyethylene/ethylene vinyl acetate (EVA) blend, polyethylene, polyester, nylon, polypropylene, thermoplastic fluorinated ethylene propylene (FEP), TFP, stainless steel, malleable metal or any combination of these materials.

The sleeve 18 may be made, for example, from one or more absorbent materials, such as a sponge-like material, that can optionally be pre-soaked in a drug solution, for example, in an antibiotic solution. In another embodiment, the sleeve 18 may be made from a non-wettable material, such as polypropylene, polyethylene, polyester, polytetrafluoroethylene (available from DuPont Corporation, Wilmington, Del., under the trademark TEFLON®)), TYVEK V, MYLAR®), or co-polymers thereof. The non-wettable materials can also be pre-treated with a therapeutically effective drug coating. The sleeve 18 can be transparent so that an operator will be able to see the implantable sling 16 inside the sleeve 18.

Figure 5A:
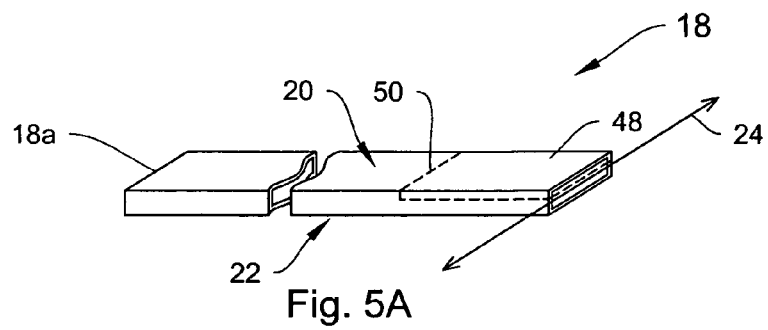
FIGS. 5A-5C schematically depicts an illustrative process for assembling the sling delivery system of FIG. 1.
Figure 5B:
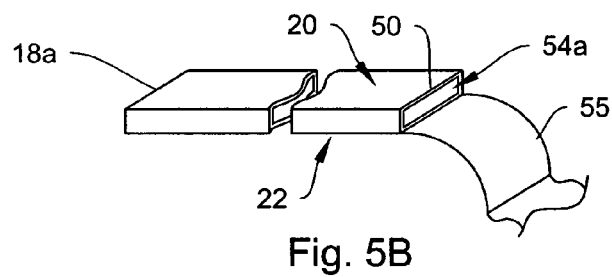
Figure 5C:
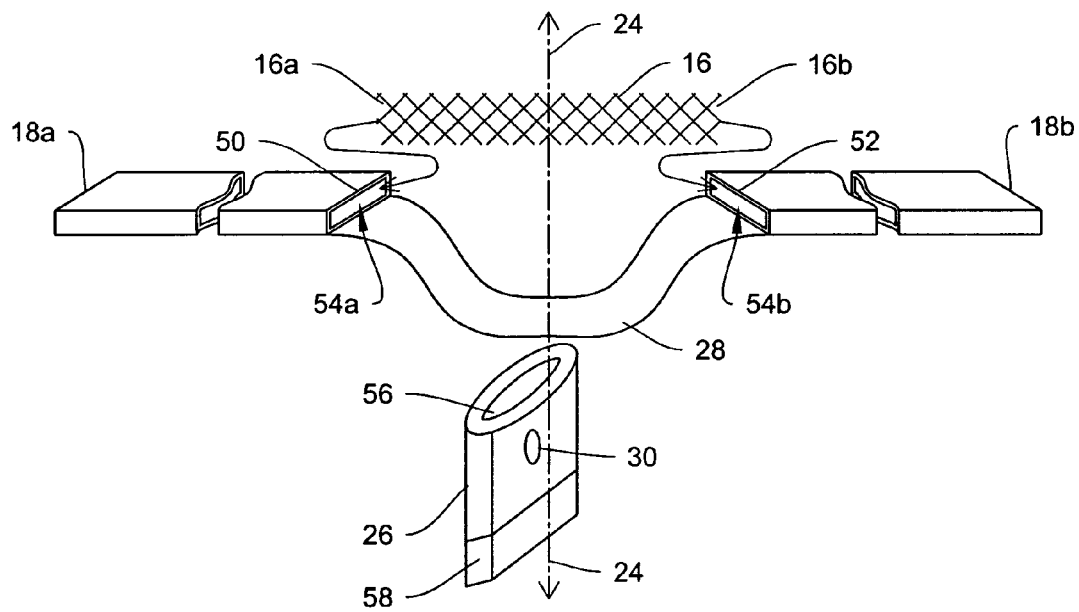

FIG. 5 shows schematically an exemplary process for assembling the sling assembly 14. As shown in FIG. 5A, beginning at the center line 24, a portion 48 of the top surface 20 of the sleeve 18 is stripped off to an edge 50 to create the gap 19 in the top surface 20 shown in FIG. 4. As shown in FIG. 5B, in the case where the sleeve 18 is formed as two sleeve halves, the procedure of FIG. 5A, results in sleeve tail portions 55. In the case of the sleeve 18 being formed with a unitary lower surface 22, the procedure of FIG. 5A results in forming the first half of the looped portion 28, shown in FIG. 5C. The same process is repeated by stripping of a similar section of the upper surface 20 of the sleeve 18 to an edge 52. As shown in FIG. 5C, the sling end 16a is then inserted into the respective lumen 54a formed between the upper 20 and lower 22 surfaces of the sleeve 18. Similarly, the sling end 16b is inserted into the lumen 54b. Then, the looped portion 28 or the tail portions 55, as the case may be, are inserted into an opening or slot 56 in the tabbed spacer 26. The tabbed spacer 26 can be fastened to the looped portion 28 or the tail portions 55, as the case may, through, for example, heat bonding, an adhesive, a fastener such as a staple, or other suitable mechanism. Preferably, the fastening occurs in the connecting region 58 of tabbed spacer 26. As mentioned above, the tabbed spacer 26 may include a center aperture 30, which can aid the medical operator in the removal of the sleeve 18, as described below. As indicated in FIG. 5C, the connecting region 58 is preferably located below the aperture 30, leaving the looped portion 28 (or tail sections 55) unattached to the tabbed spacer 26 above the aperture 30. Preferably, the tabbed spacer 26 does not enclose or attach in any way to the sling 16. Other examples of tab-like structures, which may be part of the sleeve 18 or an external part, for assisting the separation of the sleeve 18, are disclosed in commonly assigned U.S. patent application Ser. No. 10/093,371, the contents of which are incorporated herein by reference in their entirety. It should be noted that the sling assembly 14 may not require that the sleeve 18 include a tabbed spacer 26. In alternate embodiments, the sleeve 18 may include a break or rupture location (not shown), such as a perforation near the center 24, allowing the sleeve 18 to be separated after placement of the sling 16.

Figure 6:
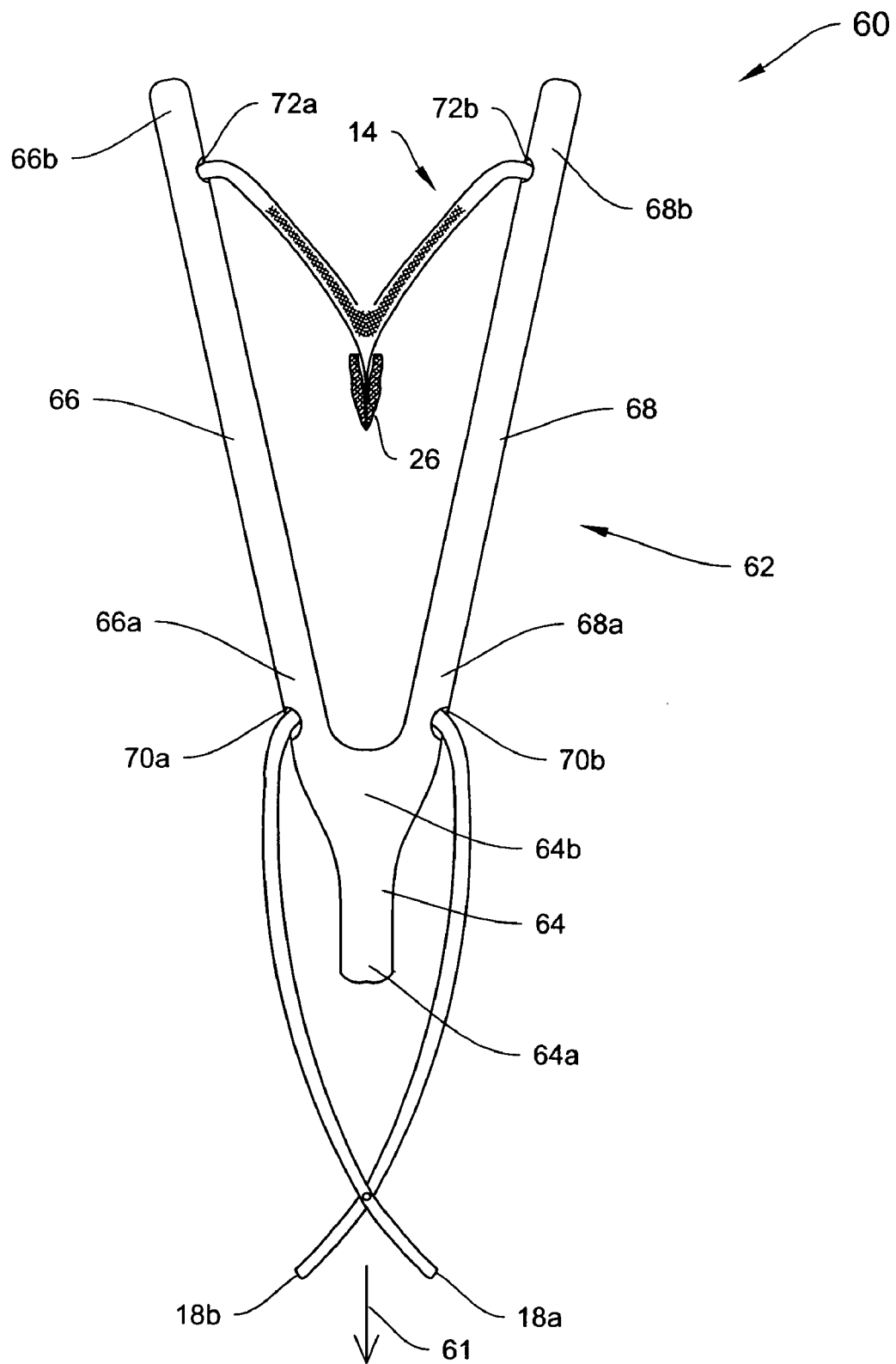
FIG. 6 depicts a sling delivery system for delivering a sling to an anatomical site of a patient according to another illustrative embodiment of the invention.

FIG. 6 shows an alternative embodiment of a sling delivery system 60. In contrast to the sling delivery system 10 of FIG. 1, which includes two delivery devices 12a and 12b, the sling delivery system 60 includes a single delivery device 62. The delivery device 62 includes a handle 64 and two delivery legs 66 and 68. As shown, the handle has a proximal end 64a (located closest to a medical operator) and a distal end 64b (located away from the medical operator. The delivery legs 66 and 68 extend from the distal end 64b of the handle 64 to form a "Y"-shaped configuration with the handle 64. The delivery leg 66 has a first side aperture 70a near its proximal end 66a, a second side aperture 72a near its distal end 66b, and defines a lumen extending between the first side aperture 70a and second side aperture 72a. Similarly, the delivery leg 68 has a first side aperture 70b near its proximal end 68a, a second side aperture 72b near its distal end 68b, and defines a lumen extending between the first side aperture 70b and second side aperture 72b. As shown, the sleeve end 18a threads through the side aperture 72a, through the lumen of the delivery leg 66 and out the side aperture 70a. Similarly, the sleeve end 18b threads through the side aperture 72b, through the lumen of the delivery leg 68 and out the side aperture 70b. The sling assembly employed with the delivery system 60 is preferably identical to the sling assembly 14 employed with the delivery system 10 of FIG. 1. Additionally, as in the case of the delivery devices 12a and 12b, the distal ends 66b and 68b of the delivery legs 66 and 68 may, for example, include end apertures in fluid communication with the respective lumens, or alternatively, taper into a tip sufficient for piercing and/or tunneling through tissue. For ease of operation the sleeve ends 18a and 18b may be connected, for example, by knotting them together. For ease of insertion into a surgical site, the distal end 64b of the handle 64 may be sufficiently flexible to enable the insertion legs 66 and 68 to be squeezed toward each other during sling placement, and sufficiently resilient to enable to insertion legs 66 and 68 to return to their rest orientation subsequent to the medical operator ceasing to apply a squeezing force. Alternatively or in addition, the insertion legs 66 and 68 may be similarly resiliently flexible.

Figure 7A:
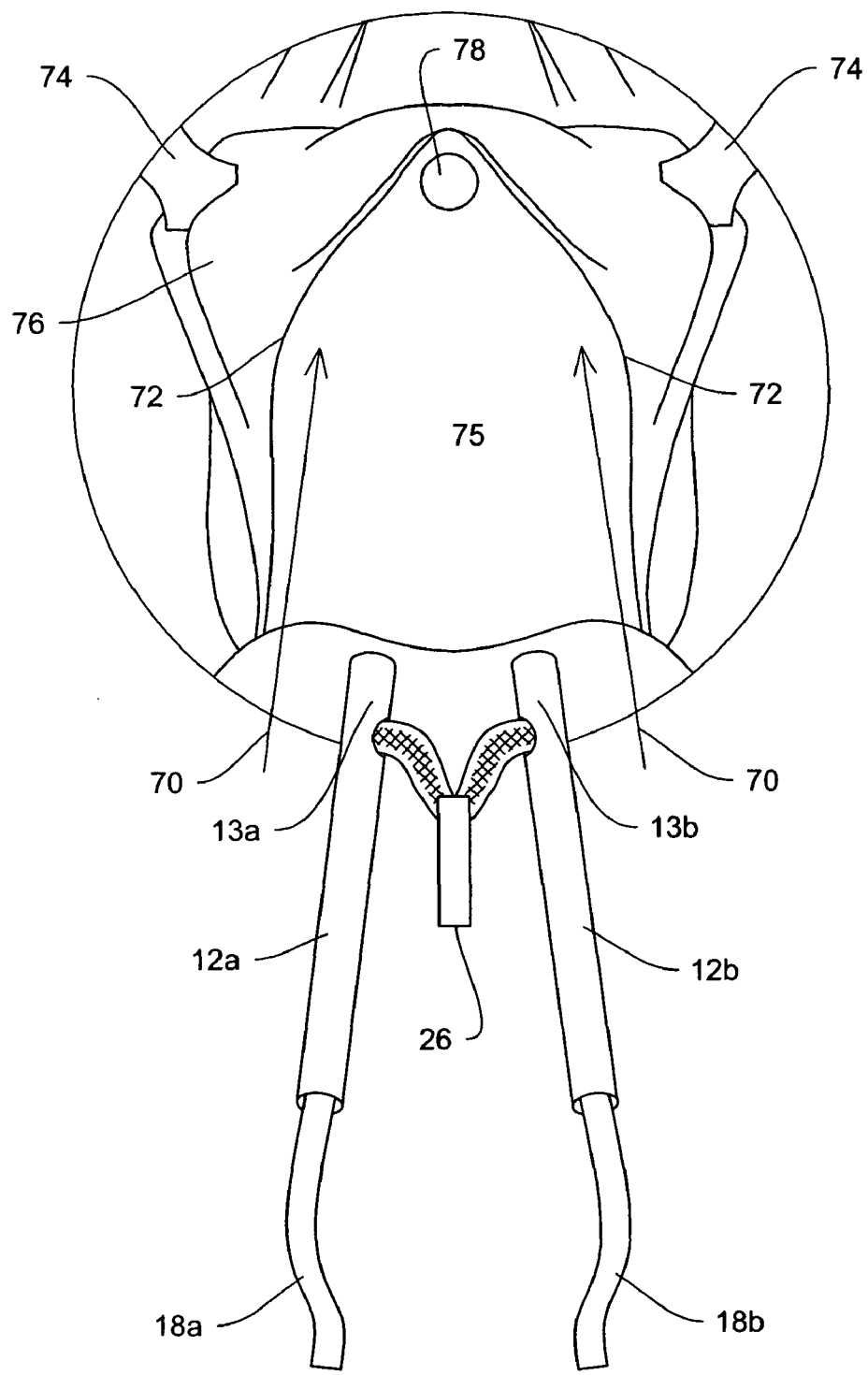
FIGS. 7A-7C schematically depict an illustrative placement of a sling at an anatomical site of a female patient using the sling delivery system of FIG. 1.
Figure 7B:
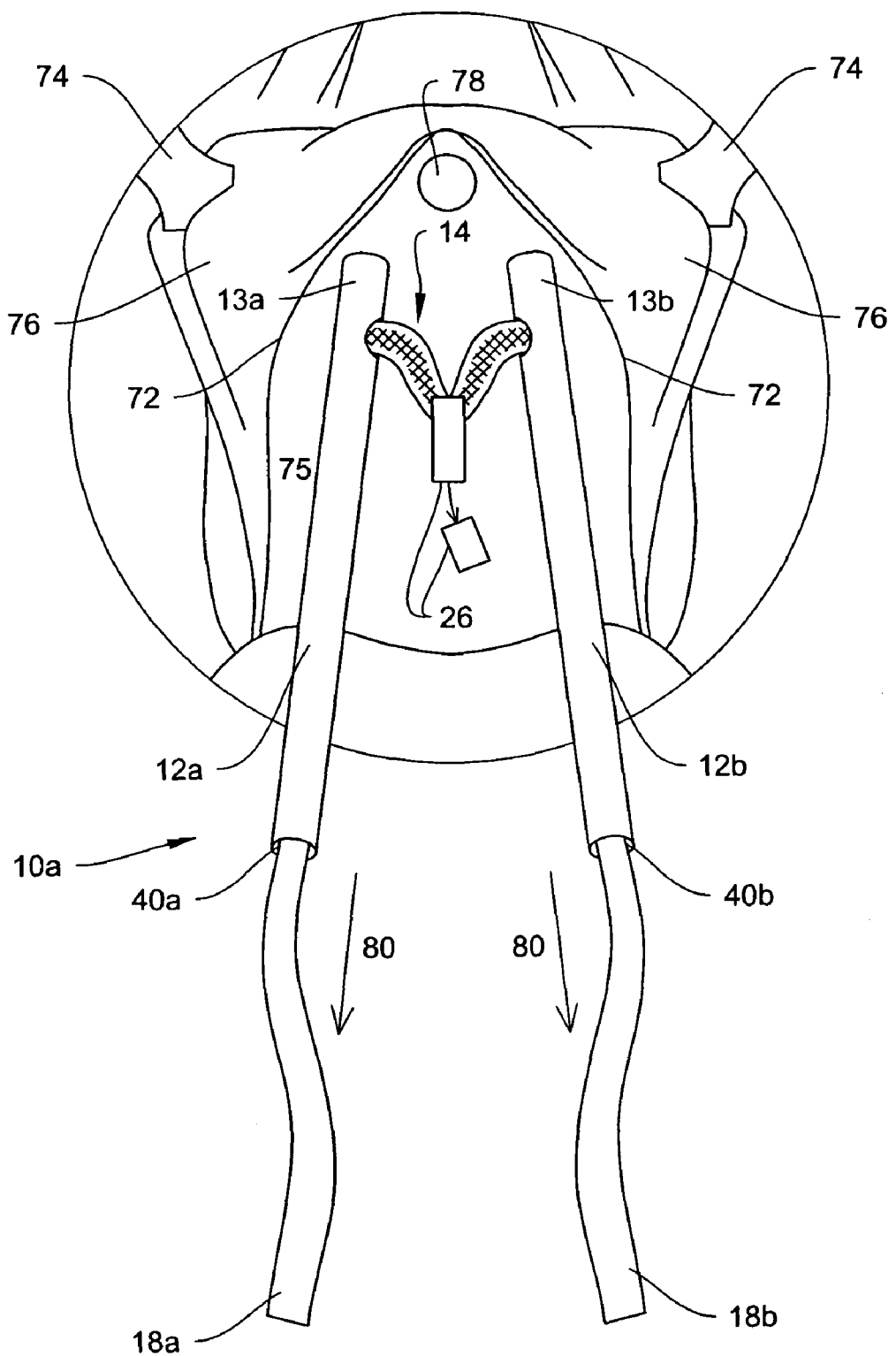
Figure 7C:
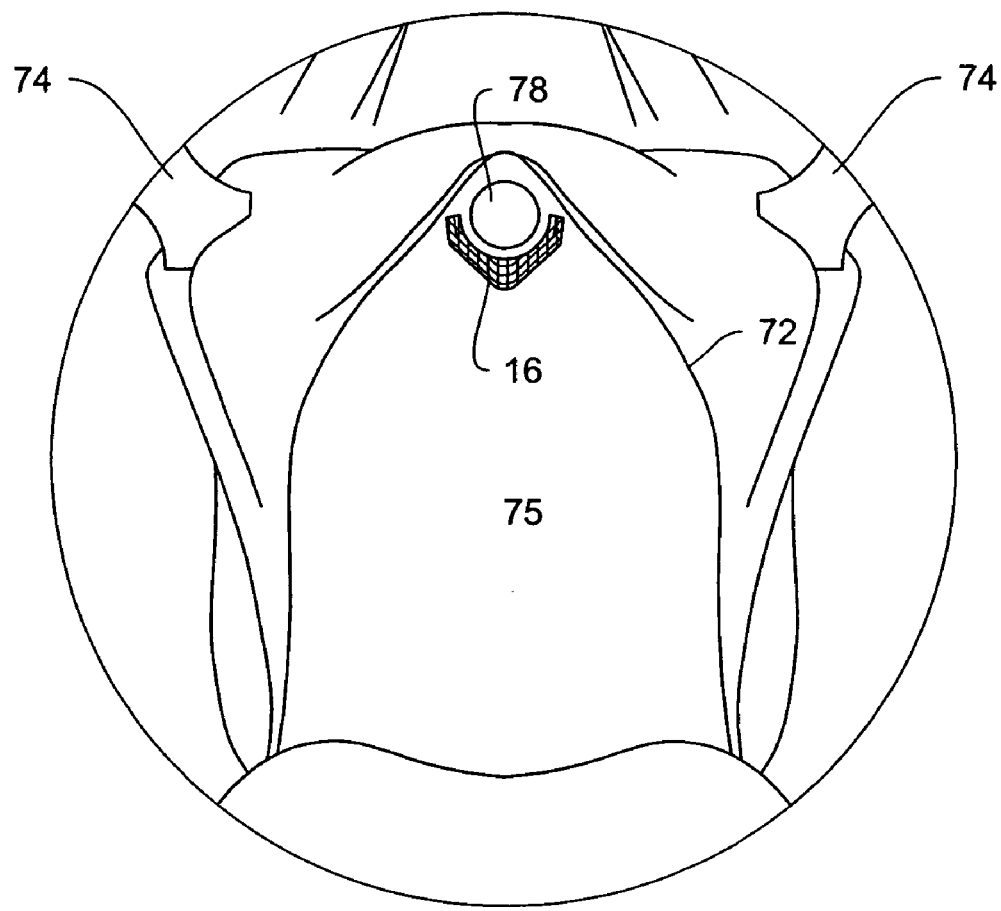

FIGS. 7A-7C illustrate an exemplary method for delivering and implanting the sling 16 to an anatomical site in a female patient using the delivery system 10 of FIG. 1, according to an illustrative embodiment of the invention. In the illustrative example, the sling 16 is placed at a midurethral location in the periurethral tissue of the patient. The method is described with reference to the sling delivery system 10 depicted in FIG. 1, but may be used with the "Y"-shaped delivery system 60 depicted in FIG. 6. Specifically referring to FIG. 7A, in the exemplary method, a mid-line incision 72 is made in the vaginal wall 76 of a patient, creating an opening 75 underneath the urethra 78. The separated vaginal tissues may be held apart by two clips 74, allowing access to the urethra 78 through the opening 75. The operator first introduces, into the vaginal opening 75, the distal ends 13a and 13b of the sling delivery devices 12a and 12b, including the sling assembly 14 threaded through the two delivery devices 12a and 12b. The operator then advances the sling delivery system 10 through the opening 75 substantially in the direction indicated by arrows 70 towards the urethra 78. Tunnels in the periurethral tissue may be previously made, or the medical operator may perform the tunneling using delivery devices 12a and 12b. The middle portion of the sling assembly 14 may be advanced along with the delivery devices 12a and 12b, or may be raised towards the urethra 78 later by pulling the sleeve ends 18a and 18b. The tab 26 may serve as an indicator of the position of the sling assembly 14 relative to the urethra 78.

Referring now to FIG. 7B, after the operator has passed the sling assembly 14 through the opening 75 in the vaginal wall 76, the distal ends 13a and 13b of the delivery devices 12a and 12b can be moved upward on either side of the urethra 78 from below. Markings may be placed on the delivery devices 12a and/or 12b to assist the operator in estimating or confirming how far the delivery devices 12a and/or 12b have advanced and if the sling 16 of sling assembly 14 has reached, for example, the mid-urethral target anatomical site. A marking near the center of the sleeve 18 and/or the position of the tab 26 can also help the operator decide when the sling 16 has reached the desired periurethral tissue for implantation and placement.

To adjust the position of the sling 16 in relation to the target tissue, the operator may manipulate the two delivery devices 12a and 12b, and/or pull on the sleeve ends 18a and/or 18b. Further, the operator may guide other medical instruments, such as forceps or scissors (not shown), through the delivery devices 12a and 12b into the space 76, for example, to adjust the position of or the tension in the sling 16 and/or to cut the sling 16. After the operator is satisfied with the position of the sling 16, the operator can separate the tab 16, for example, by cutting across the aperture 30, or otherwise separate the sleeve 18 into two sleeve sections to slide them off the sling 16. Once the tabbed spacer 26 is cut, the operator can remove it from the sleeve 18 and from the surgical site, such as the vaginal canal.

Still referring to FIG. 7B, after the tabbed spacer 26 is cut, the operator can slide the sleeve 18 off the sling 16 by pulling the sleeve ends 18a and 18b. In this way a portion of the sleeve 18 is pulled through lumen 36a and the aperture 40a of the delivery device 12a and a portion is pulled through the lumen 36b and the aperture 40b of the delivery device 12b in the directions indicated by the arrows 80. To firmly position the sling 16 in the target anatomical site, e.g., the periurethral tissues, without requiring additional sutures, the operator may need to insert or press the distal ends 13a and 13b of the delivery devices 12a and 12b deeper into the anatomical site toward the pubic bone of the patient. The tanged edges 34 of sling 16 will then embed and anchor in the tissue, so that the sling 16 will remain secured at the anatomical site when the sleeve 18 is withdrawn through the delivery devices 12a and 12b.

The medical operator needs to exercise care that the sling 16 has the appropriate tension to serve its remedial purpose, for example, by providing needed suspension to the urethra or bladder neck, or by applying tension to the periurethral tissues, e.g., the urethral sphincter. For example, if there is excessive friction between the sling 16 and the interior wall of the sleeve 18, then the sling 16 may be overtensioned and may stretch, causing the sling 16 to wrap too tightly around the target periurethral tissues or causing distortion in the sling 16, for example, curling of sides of the sling 16 along its length. To avoid over-tensioning the sling 16, one or more medical instruments, such as a pair of forceps or scissors (not shown), may initially be inserted between the urethra 78 and the sling 16 in the space 76, as discussed earlier. Then, the distal ends 13a and 13b of the delivery devices 12a and 12b may be inserted into the periurethral tissues to wrap the middle portion of the sleeve 18 snugly around the instrument and the periurethral tissues. Then, either before or after sliding the sleeve 18 off the sling 16, the medical instrument is also withdrawn to provide some slackness to counter any over-tensioning between the sling 16 and the periurethral tissue. In any case, the operator may wish to ascertain that the sleeve 18, with sling 16, is placed properly around the underside of the urethra 78 before initiating the separating and withdrawal of the sleeve 18.

Because the delivery devices 12a and 12b are still in place after the sleeve is withdrawn, the operator can use the distal ends 13a and 13b of the delivery devices 12a and 12b, which preferably are blunt and solid, to further adjust the tension in the sling 16, for example, by pressing the sling 16 deeper into periurethral tissues after the medical instrument that served as a tension buffer is withdrawn. As mentioned above, the tangs 34 on the mesh sling 16 help to immobilize the sling 16 against the periurethral tissue.

Referring now to FIG. 7C, after the operator is satisfied with the placement of the sling 16 below the urethra 78, the operator withdraws the delivery devices 12a and 12b from the vaginal canal, leaving the sling 16 in the mid-urethral position shown in FIG. 7C. The operator can then release the clips 74 and suture up the opening 75 in the vaginal wall 76. Using the device and method of the invention, the operator can complete the delivery and placement of the vaginal sling in an exclusively transvaginal fashion without resorting to any abdominal incision or cut.

The above procedure may similarly be performed with the "Y"-shaped delivery device 60 shown in FIG. 6. In that case, after cutting the tabbed spacer 26 as described above, both segments of the sleeve 18 can be slid off the sling 16 and withdrawn from the patient simultaneously, in one motion, by pulling the connected ends 18a and 18b in the direction indicated by the arrow 61 while holding the handle 64. However, the ends 18a and 18b need not be connected, and even when connected, can be pulled out of the respective openings 70a and 70b one at a time.

It should be noted that in the procedure of FIGS. 7A-7C, the sling ends 16a and 16b may be guided, for example, to a location in front of the pubic bone (i.e., to a pre-pubic location) or to a location behind the pubic bone (i.e., a suprapubic location). Additionally, the sling ends 16a and 16b may fall short of reaching the pubic bone or may extend far enough to be looped over the pubic bone, in either a pre- or suprapubic fashion. As discussed below with regard to FIGS. 12A-13, in other illustrative embodiments, each of the sling ends 16a and 16b may be placed near or fed through a respective obturator foramen.

Figure 8A:
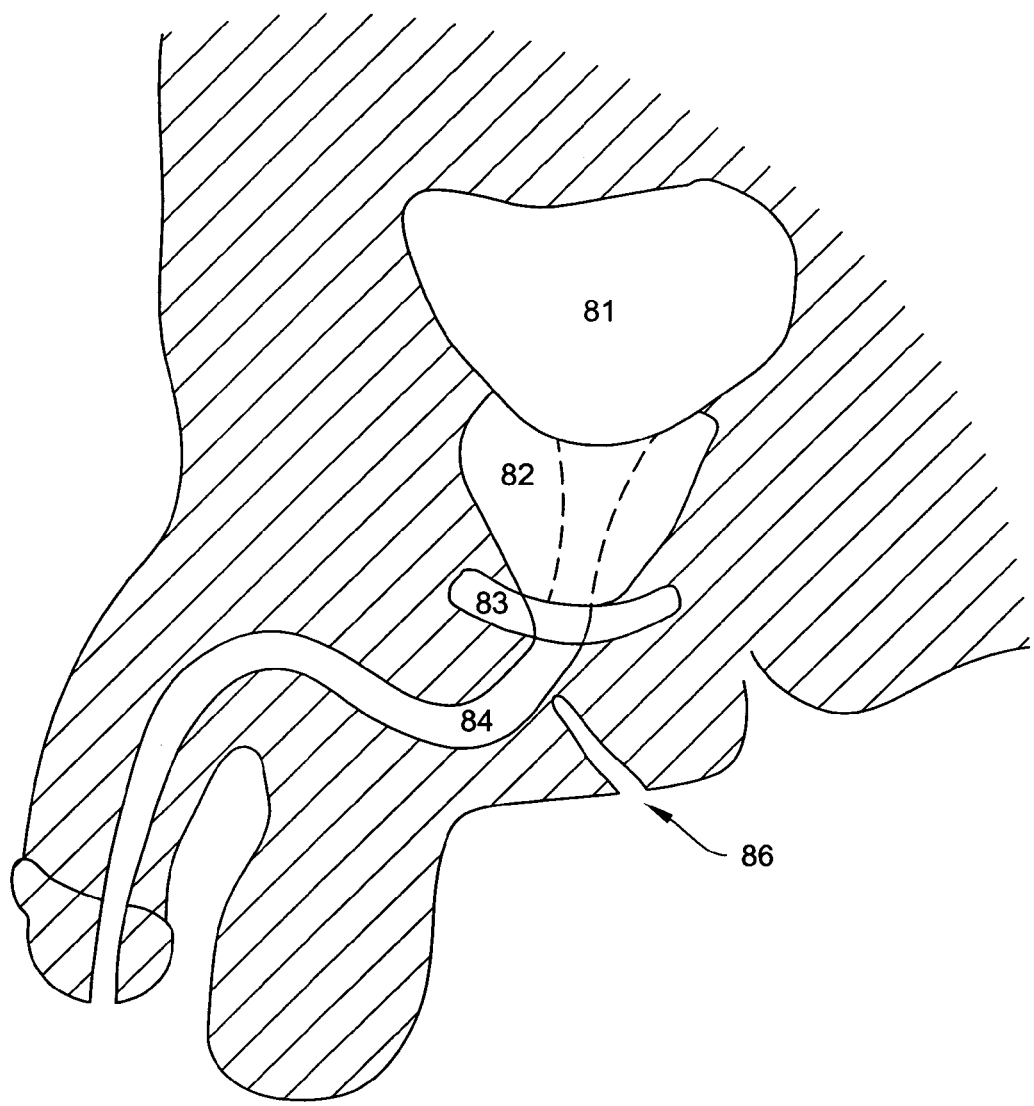
FIGS. 8A-8C schematically depict an illustrative placement of a sling at an anatomical site of a male patient using the illustrative sling delivery system of FIG. 1.
Figure 8B:
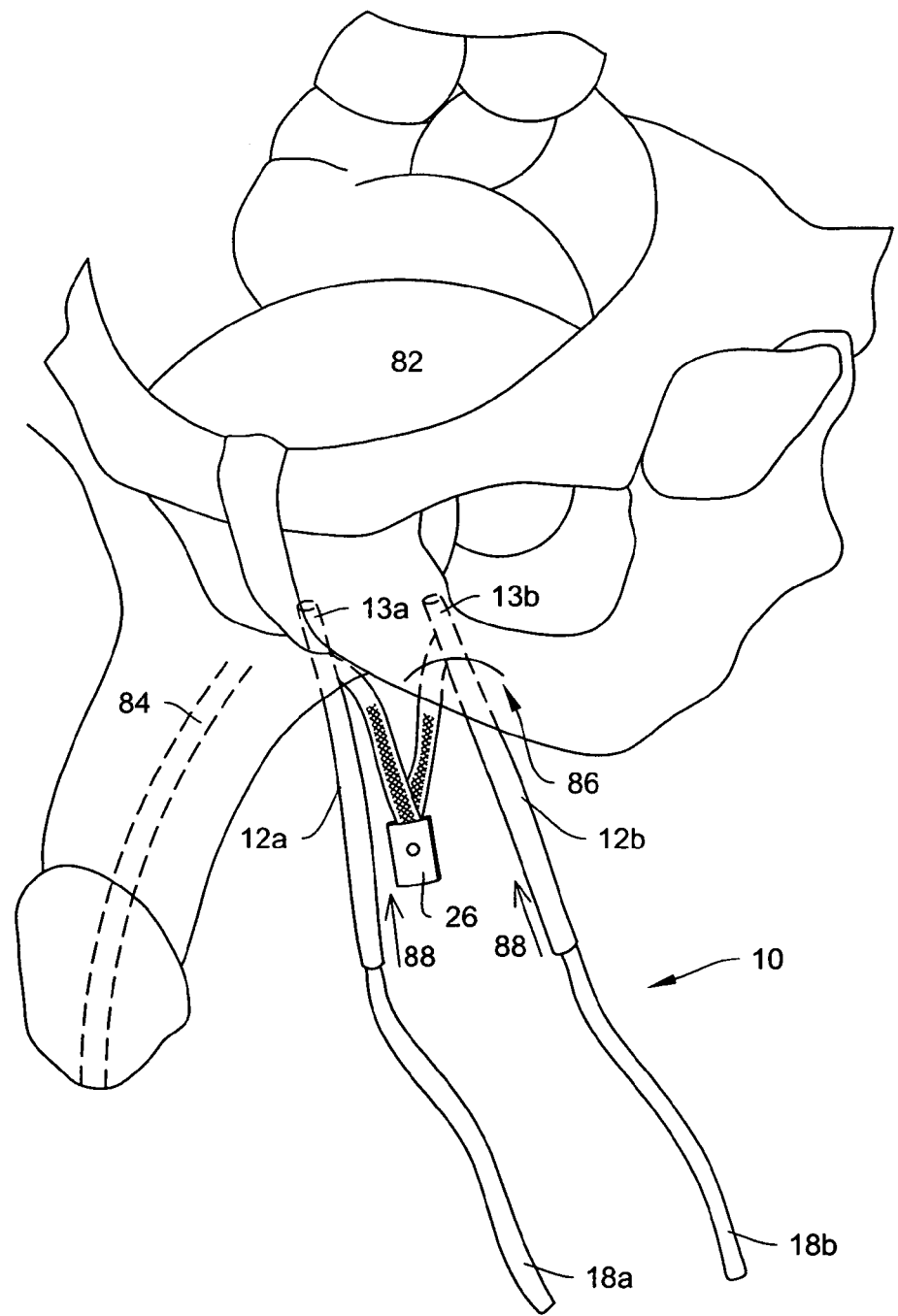
Figure 8C:
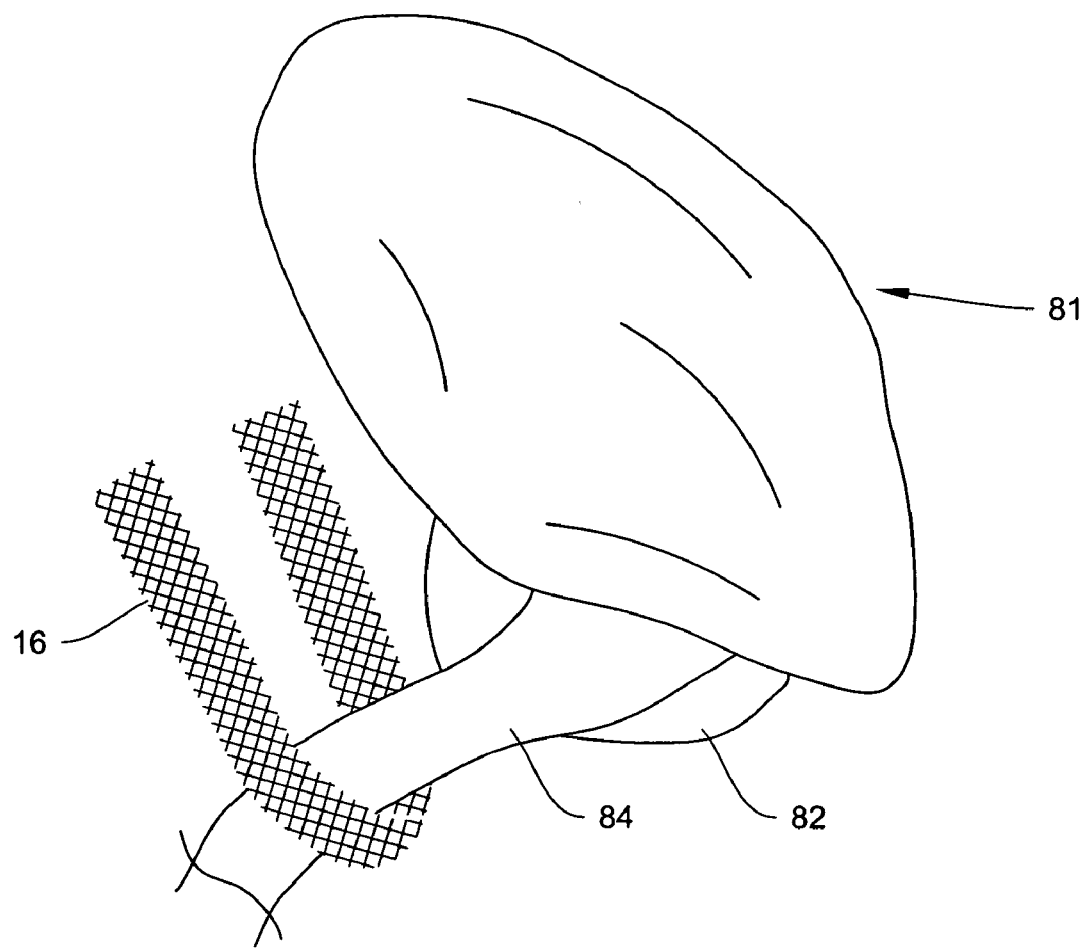

FIGS. 8A-8C illustrate an exemplary method for delivering and implanting the sling 16 to an anatomical site in a male patient using the delivery system 10 of FIG. 1, according to an illustrative embodiment of the invention. FIG. 8A schematically shows the urogenital region of a male patient, illustrating the anatomical relationship between the bladder 81, the prostate 82, the sphincter 83, and the urethra 84. In the exemplary method, a small incision 86 is made in the perineal area of the patient, creating an opening underneath the urethra 84. Referring now to FIG. 8B and also back to FIG. 1, the operator first introduces into the incision 86 the distal ends 13a and 13b of the sling delivery devices 12a and 12b, including the sling assembly 14 threaded through the two delivery devices 12a and 12b. The operator then advances the sling delivery system 10 through the incision 86 substantially in the direction indicated by arrows 88 towards the urethra 84. As described above with reference to FIGS. 7A-7C for a female patient, the medical operator may perform the tunneling using delivery devices 12a and 12b, or tunnels in the periurethral tissue may be previously made. The middle portion of the sling assembly 14 may be advanced along with the delivery devices 12a and 12b, or may be raised towards the urethra 84 later by pulling the sleeve ends 18a and 18b. The tabbed spacer 26 may serve as an indicator of the position of the sling assembly 14 relative to the urethra 84. The procedure of implanting the sling 16, including adjusting the position of the sling 16, adjusting the tension in the sling 16, and sliding the sleeve 18 off the sling 16 subsequent to cutting the tabbed spacer 26 at the level of aperture 30, is similar to that described above with reference to FIGS. 7A-7C for a female patient.

Referring now to FIG. 8C, after the operator is satisfied with the placement of the sling 16 below the urethra 84, the operator withdraws the delivery devices 12a and 12b from the incision 86, leaving the sling 16 in the urethral position shown in FIG. 8C. The operator can then suture up the incision 86 made in the perineal area. Using the device and method of the invention, the operator can complete the delivery and placement of the sling 16 without resorting to any abdominal incisions or cuts.

The above procedure may similarly be performed with the "Y"-shaped delivery device 60 shown in FIG. 6, as described above with reference to FIGS. 7A-7C. Alternatively, the procedure may be performed using other delivery device embodiments discussed below with reference to FIGS. 9A-13. It should be understood that for the described procedures, and other procedures using the described devices and systems, the delievery devices and sling may be tailored, for example, in the dimensions of the device devices, such as length, diameter, shape, and curvature, sling assembly, such as length and width of the sling or suture thread, for a particular method of delivery or for placement to a specific anatomical site.

Figure 9:
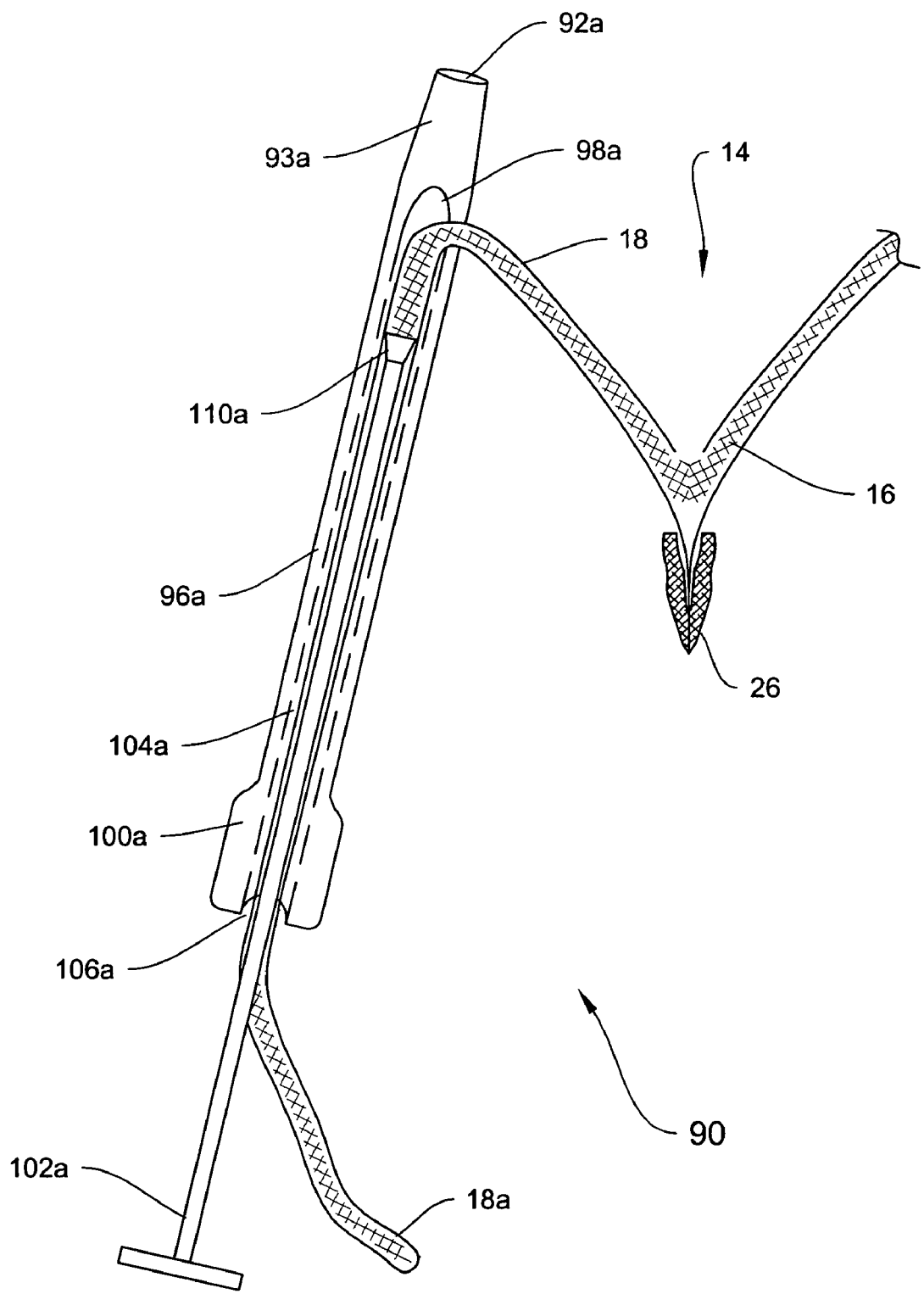
FIG. 9 depict a sling delivery system according to an alternative embodiment of the invention.

FIG. 9 shows an alternative embodiment of a sling delivery system 90 with modified delivery devices 96a and 96b and a sling assembly 14. Only the delivery device 96a is shown in FIG. 9A. The delivery device 96b is substantially identical in structure to delivery device 96a. The sling assembly 14 includes a sling 16 and a sleeve 18. Similar to the delivery devices 12a and 12b of FIG. 1, the delivery device 96a is formed as a tube or cylinder that defines at least one lumen. In one illustrative embodiment, a lumen 104a extends from a radial aperture 98a to an end aperture 106a. The delivery device 96a may also taper towards the distal end 92a and may terminate as a conical tip sufficient for dilation and tunneling through the tissue. The delivery device 96a may be straight, curved or have a combination of straight and curved sections.

Unlike the delivery devices 12a and 12b shown in FIG. 1, the delivery devices 96a and 96b each include cutting devices 110a, for example, in form of a blade, and can have a handle 100a. The cutting device 110a is depicted in FIG. 9A and is shown as located inside the lumen 104a, preferably near the radial aperture 98a. However, the cutting device 110a and the actuator 102a may be located in a second lumen extending between the radial aperture 98a and the end aperture 106a. The cutting device 110a is operatively connected to an actuator 102a and can be operated by pushing the actuator 102a towards the handle 110a.

The sling delivery system 90 may be used for delivering and implanting the sling 16 to an anatomical site in a patient, both female and male, in a substantially identical process as to that described above with reference to FIGS. 7A to 8C. Once the delivery devices 96a and 96b are in position along either side of the urethra and the sling assembly 14 is properly positioned in relation to the anatomical site in the patient, the tabbed spacer 26 is cut to allow sleeve 18 to slide off the sling 16. After a section of the sleeve 18 has been pulled out of the lumen 104a through the end aperture 106a in a similar fashion to that described with respect to sling delivery systems of FIG. 1 and FIG. 5, the sling 16 can be cut by blade 110a and the delivery devices 96a and 96b may be withdrawn from the surgical site as before. It is to be understood that other surgical instruments, such as forceps or scissors, may also be used during the procedure.

Figure 10:
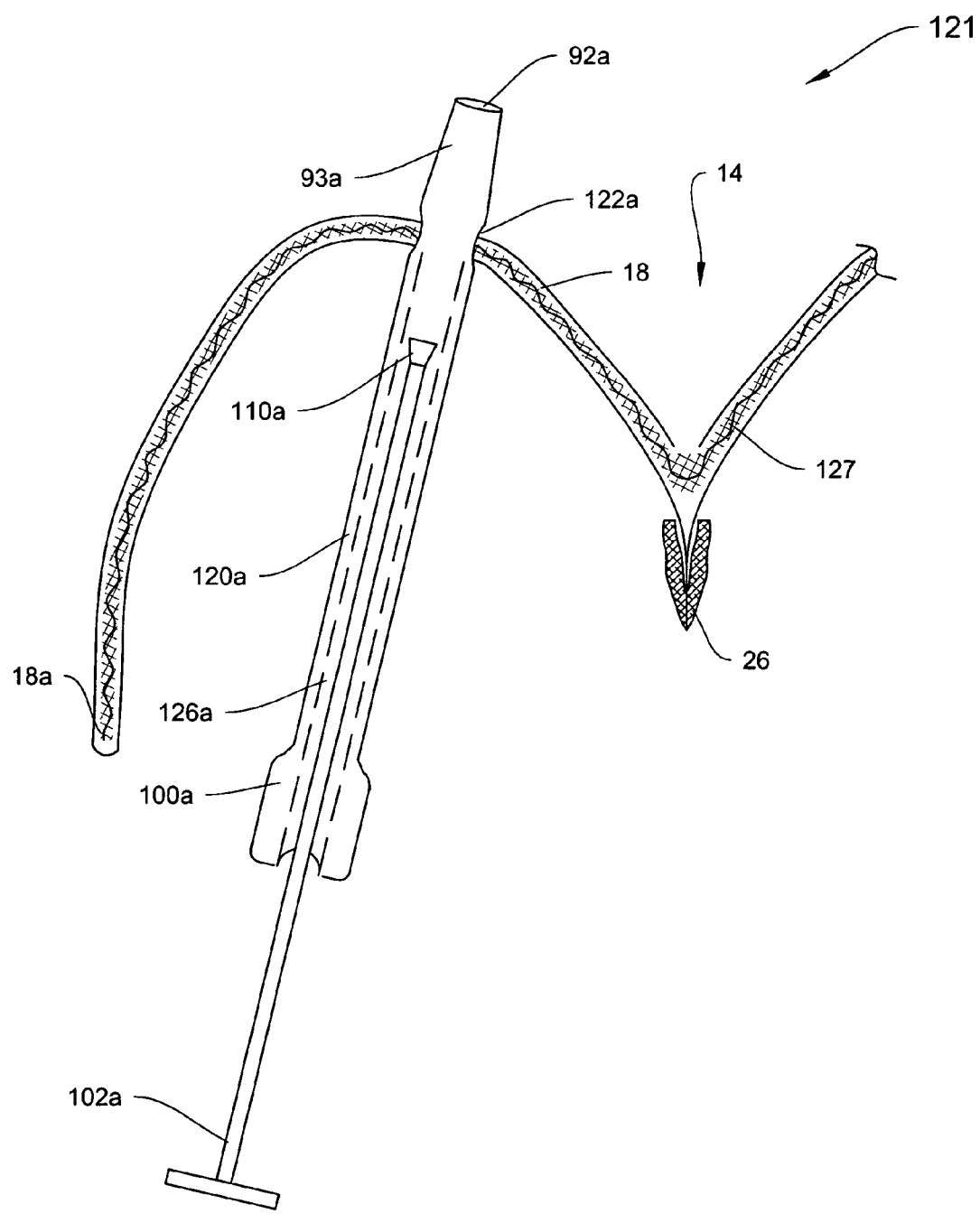
FIG. 10 depicts a sling delivery system according to another alternative embodiment of the invention.

FIG. 10 shows an alternative embodiment of a sling delivery system 121 including delivery devices 120a and 120b. The second delivery device 120b (not shown) is substantially identical to delivery device 120a. Delivery device 120a includes a cutting device 110a similar to that described above with reference to FIG. 9. The cutting device 110a is also connected to an actuator 102a extending through the lumen 126a and operated by pushing the actuator towards the handle 100a. However, the sleeve 18 is here not threaded through the lumen 126a, but is instead threaded through a radial aperture 122a extending transversely through the distal end 93a of the delivery device 120a. The sling delivery system 121 may be used for delivering and implanting the sling 16 to an anatomical site in a patient, both female and male, in a substantially identical process as to that described above with reference to FIGS. 1, 5 and 9. Once the delivery devices 120a and 120b are in position along side the urethra and the sling assembly 14 is properly positioned in relation to the anatomical site in the patient, the tabbed spacer 26 is cut to allow sleeve 18 to slide off the sling 16. The sling 16 is depicted as having a suture thread 127 extending through the sling 16. The suture 127 can prevent the sling 16 from stretching or distorting when the sleeve 18 is slid off sling 16 after the tabbed spacer 26 is cut. The operator pulls the separated section of the sleeve 18 through the aperture 122a, and then cuts the sling 16 with the blade 110a. The delivery devices 120a and 120b are withdrawn from the surgical site as before. In an alternative embodiment, the sleeve 18 may be made from bioabsorbable materials. When sleeve 18 is bioabsorable, sleeve 18 does not include a tabbed spacer 26. The sleeve 18 functions to facilitate placement of the sling 16 at an anatomical site. After the medical operator determines that the sleeve 18 and the sling 16 are placed as desired, the medical operator may cut the sleeve 18 and the sling 16 with the blade 110a. Although FIG. 10 depicts sling 16 as extending substantially the length of the sleeve 18, the sling 16 may have a length substantially shorter than the length of the sleeve 18. For example, the sling 16 may not be threaded through the aperture 122a and is not cut by the blade 110a along with sleeve 18.

Use of a bioabsorable sleeve 18 may provide an additional protection against the distorting or deforming of sling 16 by the application of too much tension. Examples of bioabsorbable sleeves, and examples of materials for making such sleeves, are disclosed in commonly assigned U.S. patent application Ser. No. 10/631,364, the contents of which are incorporated herein by reference in their entirety. The sling assemblies described herein may be modified to include a bioabsorable sleeve.

Figure 11:
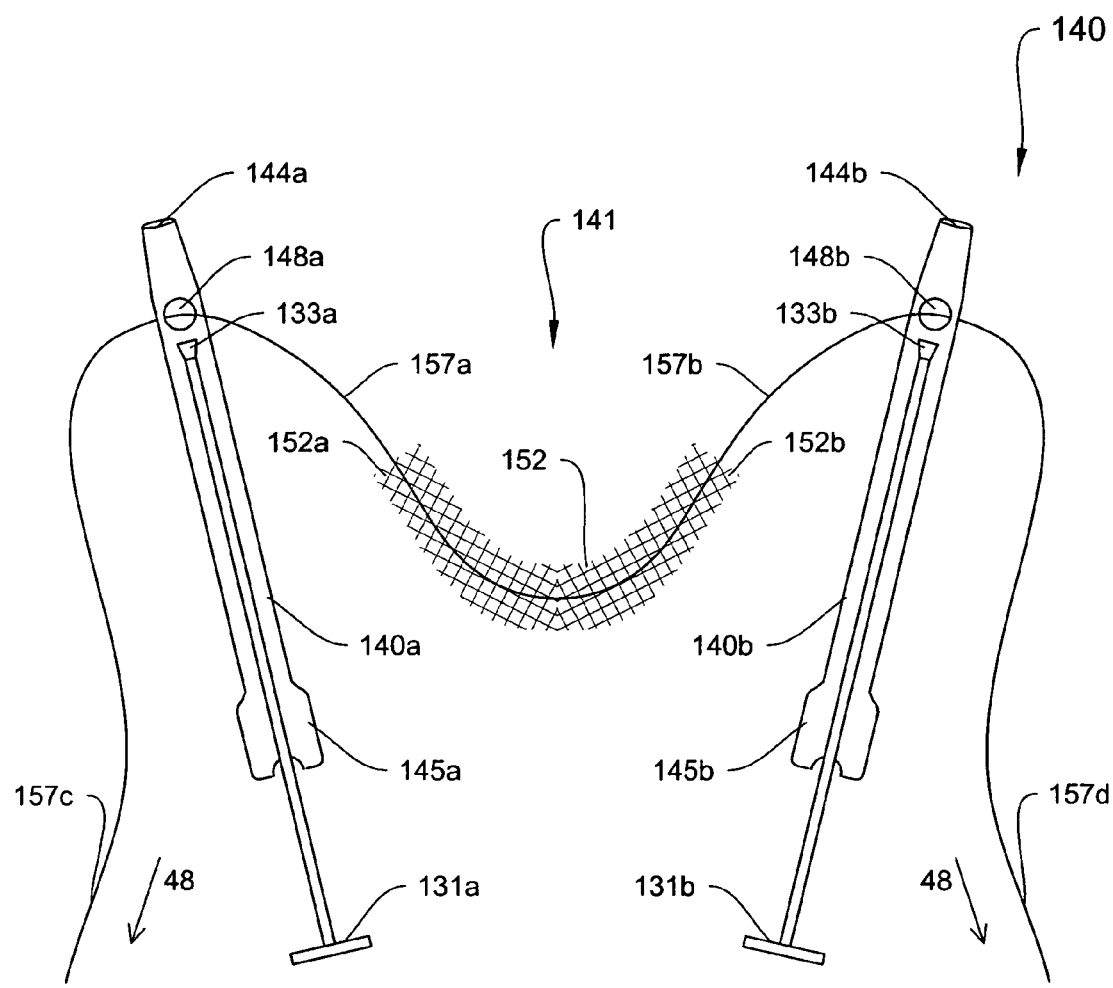
FIG. 11 depicts a sling delivery system according to another alternative embodiment of the invention.

FIG. 11 shows another alternative embodiment of a sling delivery system 140 with delivery devices 140a and 140b and cutting devices 133a and 133b similar to those depicted in FIG. 10. The delivery devices 140a and 140b have radial apertures 148a and 148b extending transversely through the distal ends 144a and 144b of the delivery devices 140a and 140b. The sling delivery system 140 includes a sling assembly 141, which includes a sling 152 that, unlike the sling 16, is not enclosed by a sleeve 18. In the exemplary embodiment depicted in FIG. 11, the sling ends 16a and 16b are attached to respective sutures 157a and 157b, which are threaded through the radial apertures 148a and 148b of the delivery devices 140a and 140b. For delivering and implanting the sling 16 in a patient, the operator places the delivery devices 140a and 140b at the surgical site, as described above with reference to FIGS. 1-10 and adjusts the tension of sling 152 by pulling the suture ends 157c and 157d in the direction indicated by arrows 48. When the sling 152 is properly placed, the operator cuts sutures 157a and 157b with the blades 133a and 133b, leaving the sling 152 in place.

The sutures 157a and 157b can extend over a partial or the entire length of the sling 152. In such a configuration, the sutures 157a and 157b can prevent the sling 152 from stretching or distorting when the sling 152 is tensioned from suture ends 157c and 157d.

Figure 12:
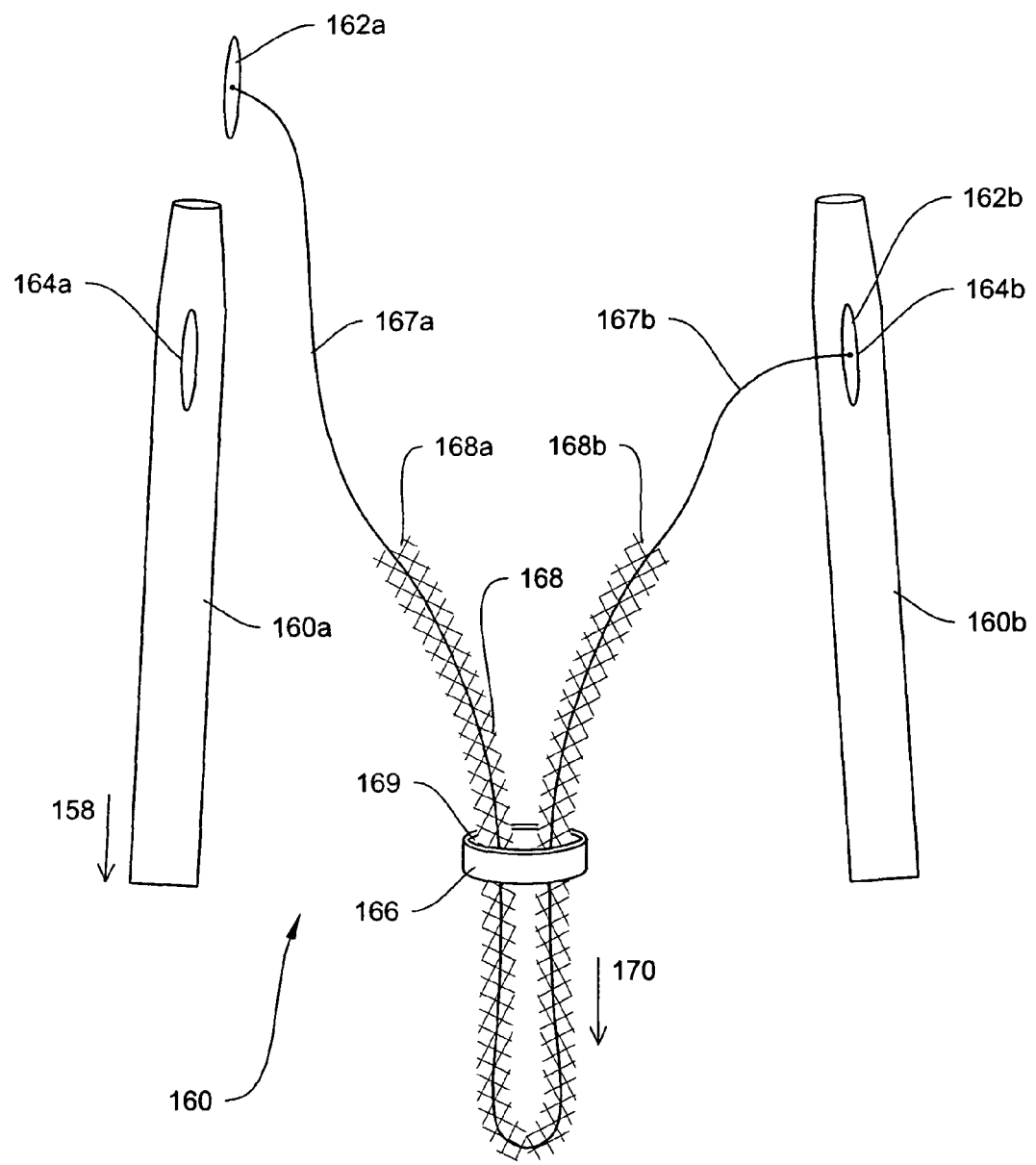
FIG. 12 depicts a sling delivery system according to another alternative embodiment of the invention.

FIG. 12 shows another alternative embodiment of a sling delivery system 160 which also uses a sling 168 not enclosed by a plastic sleeve. The sling 168 is affixed by the sling ends 168a and 168b to suture sections 167a and 167b. Unlike in the embodiment previously described with reference to FIG. 11, the suture sections 167a and 167b have fixed lengths and are provided with end connectors 162a and 162b. The slots 164a and 164b are disposed on the delivery devices 160a and 160b near the respective distal ends and releasably engage with end connectors 162a and 162b. The sling 168 loops though a lumen 169 of a fastener 166, for example, the ring 166 depicted in FIG. 12. The fastener 166 may be used to tension the sling from the center portion of the sling 168 in contrast to the tensioning methods described above which tension other sling embodiments from the sling ends.

The delivery devices 160a and 160b can be formed as tubes or cylinders, and can be straight, curved, or have a combination of straight and curved sections. The delivery devices 160a and 160b can be hollow or solid and can have blunt, rounded or conical distal ends.

The medical operator may insert the end connectors 162a and 162b into corresponding slots 164a and 164b, or the sling delivery system 160 may be supplied preassembled. The medical operator then inserts the delivery devices 160a and 160b into the surgical site in a manner described above with respect to FIGS. 7A-11. After the sling assembly 160 is suitably positioned and anchored in the periurethral tissue, the operator withdraws the delivery devices 160a and 160b from the surgical site in the direction indicated by arrow 158, thereby also disengaging the end connectors 162a and 162b from the slots 164a and 164b. The connectors 162a and 162b may disengage from the slots 164a and 164b due to friction between the connectors and the body tissues or be pushed out of the slots 164a and 164b by push rods (not shown). The medical operator can then adjust the length and tension of the sling by pulling the sling 168 through the lumen 169 of ring 166 in the direction indicated by arrow 170. Since the ring 166 and the end connectors 162a and 162b remain in the patient's body, they are made of a biocompatible material.

Figure 13:
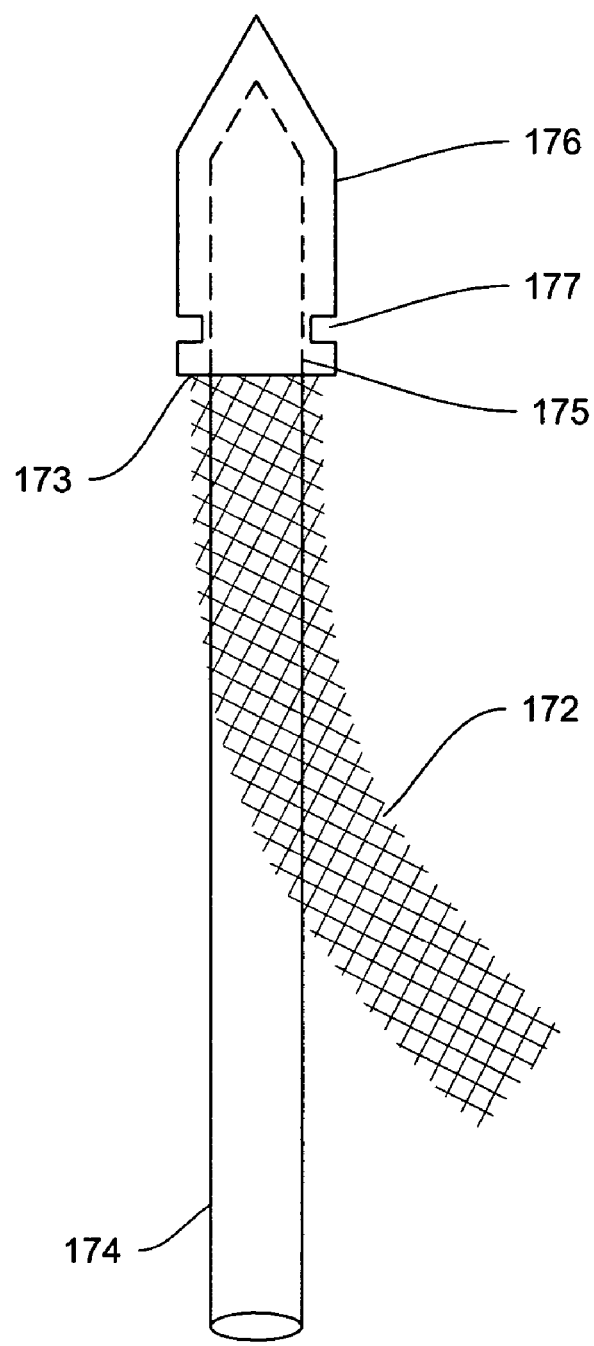
FIG. 13 depicts a sling delivery system according to another alternative embodiment of the invention.

FIG. 13 shows a different embodiment of an end connector, e.g., a dilator 176, attached to sling 172 at a junction 173. The dilator 176 preferably has the same width as the sling 172, so that the sling 172 lies flat when advanced to the surgical site. The dilator 176 can be inserted into the surgical site in the same manner as the connectors 162a and 162b of the sling assembly 160 of FIG. 12. The exemplary dilator 176 depicted in FIG. 13 includes a blind hole 175 into which a needle or rod 174 can be inserted. The rod 174 can be used to push the dilator 176 into the periurethral tissue to anchor the sling 172. Optionally, the dilator 176 can also have a recess 177 adapted to mate with a suitable delivery device. The rod 174 may also include a push tube inside the rod 174 or a hollow tube encasing the rod 174 to push the dilator 176 off the rod 174 to assist in disengaging the dilator 176 from the rod 174.

In a similar fashion to the sling 168 depicted in FIG. 12 and described above, the sling 172 is tensioned from the center portion instead of from its ends by utilizing a ring or other means for adjusting the length of the sling 172 from its center portion. Since the dilator 176 remains in the patient's body, it must be made of a biocompatible material.

Other examples of end portions such as the anchors and dilators described above, which may be part of the sleeve 18 or the sling 16, may include suture threads formed into loops or knots. The suture loops or knots may be carried by a knotched distal end of a delivery device and placed in the desired anatomical site of a patient. The suture loops or knots may be disengaged by withdrawing the delivery device or by using a push rod to disengage the suture loop or knot from the distal end of the delivery device. Other structures on the distal end of the delivery devices may also be used to carry the end portions, such as clamps.

Although FIGS. 11-13 illustrated the sling assemblies as sleeve-less, it should be understood that the sling assemblies described above may be modified to include a bioabsorbable sleeve. For example, the sling assembly 141, including the sutures 157a and 157b, may be enclosed by a bioabsorbable sleeve. In another example, the sling assembly of FIG. 13 may also include a bioabsorbable sleeve such that both the bioabsorbable sleeve and the sling 172 is attached to dilator 176 at the junction 173. In an alternative embodiment, the bioabsorbable sleeve may be attached to dilator 176 at the junction 173 while sling 16 has free ends and does not attach to anything.

Figure 14:
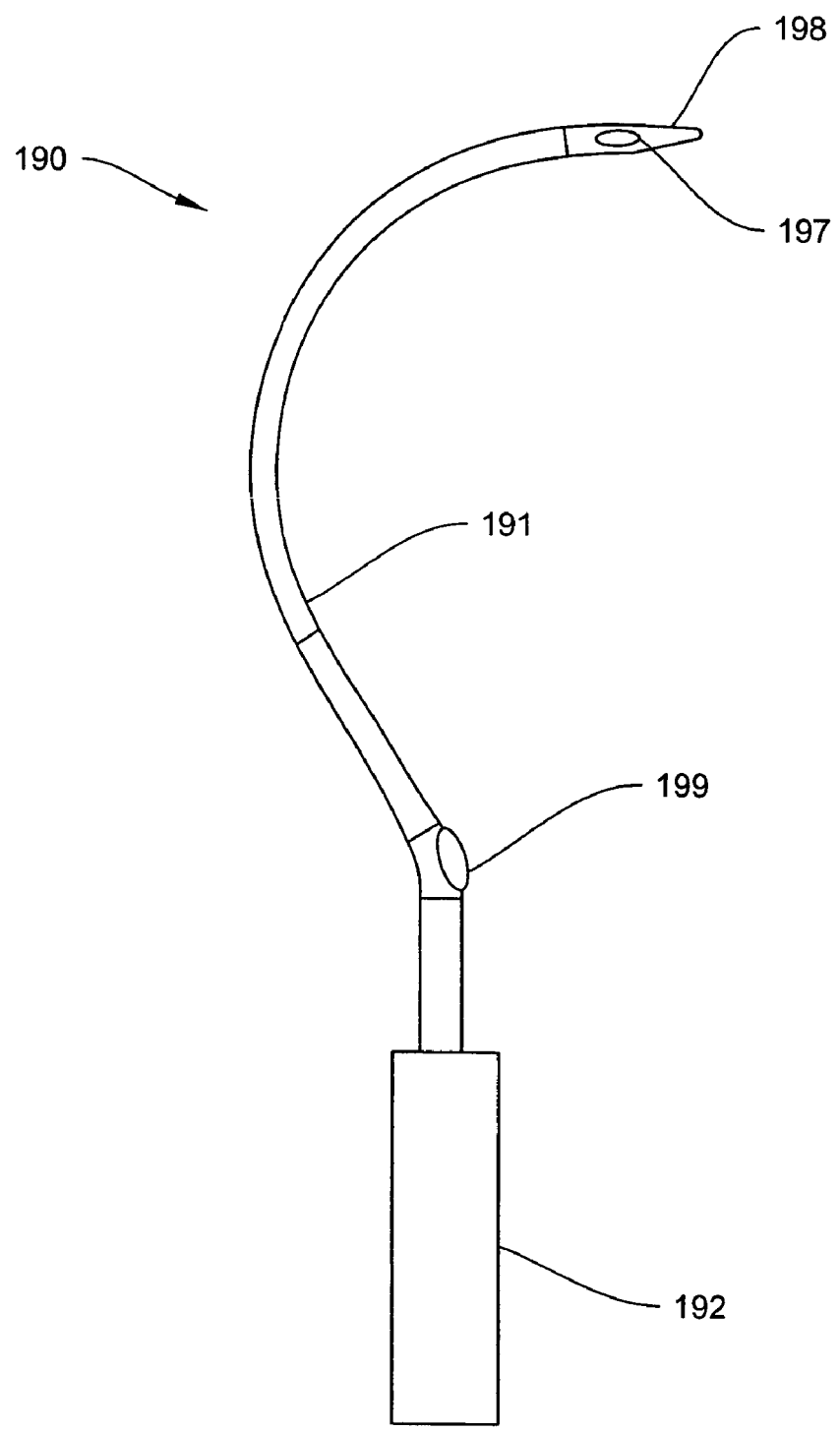
FIG. 14 shows another alternative sling delivery system for placing a sling.

FIG. 14 shows another embodiment of a delivery device 190, which includes a handle 192 and a shaft 191 located in a single plane. Like the delivery device 180, the shaft 191 of delivery device 190 can include a proximate aperture 199 and a distal aperture 197 near the distal end 198. The distal end 198 may also terminate in a conical tip. The apertures 197 and 199 can be connected by a lumen through which sleeve 18 of sling assembly 14 can be threaded. The distal end 198 of the shaft 191 can likewise be provided with connectors as described above with respect to the delivery devices 160a, 160b, and 174.

A medical operator can use the delivery device 190 for delivering and implanting the sling 16 to an anatomical site in a female or male patient. The medical operator creates with the delivery device 190 a passage through body tissue, e.g. for a female patient, from an incision in the vaginal wall toward the obturator foramen. A first delivery device is inserted upward through the vaginal wall at about 45 degrees to the vertical midline of the patient's body. Then the handle is turned upward and the delivery device is inserted toward, into, or through the obturator membrane. The process is repeated with the second (identical) delivery device on the contralateral side of the body.

As can be seen from the above illustrative description, the invention, according to one feature, provides a simplified procedure with and delivery device that reduces trauma to the patient, by avoiding any incisions other than those made in the vaginal wall. The need for cystoscopy is reduced or eliminated because this procedure minimizes the chance of threading the sling through the bladder by accident. Also, by in one embodiment, providing a pre-assembled delivery system, the invention further simplifies the procedure for a medical operator and also reduces potential source of infection from multiple pieces of equipment to one piece of equipment, which is easier and less expensive to sterilize and package.

It should also be understood that the delivery devices 190 may be modified for use with the sling assemblies depicted in FIGS. 11, 12, and 13. For example, the delivery device 190, when used with the sling assembly 141, may include an aperture extending through a distal section of the distal end 198 through which the suture 157a of the sling assembly 141 is threaded. Furthermore, the distal end 198 may include a cutting element and an actuator in the lumen in the distal end 198 and the arm 184 for cutting the suture 157a once the sling 152 is placed as desired.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A system for treating urinary incontinence in a patient, comprising:
    a first elongated delivery device having a proximal end and a distal end, a first aperture through a sidewall of the delivery device proximal to the distal end wherein the aperture is parallel to the longitudinal axis of the delivery device, a second aperture located near the proximal end, and a lumen extending between the first and second apertures,
    a sling assembly including a sling at least partially enclosed by a sleeve, the sling, assembly having a first end threaded through into the first aperture, through the lumen and out the second aperture of the first elongated delivery device, wherein the sling has a first end that extends into the lumen of the first elongated delivery device;
    an operator actuatable cutting device located in the lumen for cutting off a portion of at least one of the sling and the sleeve;
    a second elongated delivery device having a proximal end and a distal end, a first aperture located near the distal end, a second aperture located near the proximal end, and a lumen extending between the first and second apertures, and
    the sling assembly has a second end threaded through into the first aperture, through the lumen and out the second aperture of the second elongated delivery device; and a handle having proximal and distal ends, and wherein the proximal ends of the first and second elongated delivery devices intersect with the distal end of the handle to form a substantially "Y"-shaped delivery system configuration.

2. The system of claim 1, wherein the sleeve is longer than the sling and a portion of the sleeve not enclosing the sling is threaded into the first aperture, through the lumen and out the second aperture.

3. The system of claim 1, wherein the first elongated delivery device includes a conical tip as its distal end, the conical tip being sufficient to pierce and tunnel through tissue.

4. The system of claim 1, wherein the second aperture is located at a termination of the proximal end of the first elongated delivery device.

5. The system of claim 1, wherein the second aperture is located in a side wall near the proximal end of the first elongated delivery device.

6. 1, wherein the sling assembly includes a tabbed spacer located along a bottom surface of the sleeve, and the tabbed spacer engages a portion of the bottom surface of the sleeve to inhibit the sleeve from sliding off the sling, without first cutting through the tabbed spacer.

7. The system of claim 6, wherein the tabbed spacer engages a looped portion of the bottom surface of the sleeve.

8. The system of claim 6, wherein the tabbed spacer engages sleeve tails of the bottom surface of the sleeve.

9. The system of claim 1 including an actuator operatively connected to the cutting device and extending from the cutting device through the lumen and out the second aperture, the cutting device being actuated by pushing the actuator in a distal direction.

10. The system of claim 1, wherein the distal end of the first elongated delivery device has a rounded or frustoconical shape.

11. The system of claim 1, wherein the first elongated delivery device includes a handle located near its proximal end.

12. The system of claim 1, wherein the first elongated delivery device includes a shaft having a first straight portion extending distally along an axis from a distal end of the handle and a curved portion first curving away from the axis and then curving back toward the axis.

13. The system of claim 12, wherein the curved portion crosses the axis subsequent to curving back toward the axis.

14. The system of claim 1 comprising,
    a second elongated delivery device having a proximal end and a distal end, a first aperture located near the distal end, a second aperture located near the proximal end, and a lumen extending between the first and second apertures, and
    the sling assembly has a second end threaded through into the first aperture, through the lumen and out the second aperture of the second elongated delivery device.

15. The system of claim 1, wherein the proximal ends of the first and second elongated delivery devices attach to the distal end of the handle.

16. The system of claim 1, wherein the proximal ends of the first and second elongated delivery devices are formed integrally with the distal end of the handle.

17. The system of claim 1, wherein the first and second elongated delivery devices are sufficiently flexible for an operator to squeeze them together during a sling implantation procedure.

18. The system of claim 17, wherein the first and second elongated delivery devices are sufficiently resilient to substantially return to an original shape in response to the operator removing a squeezing force.

19. The system of claim 1, wherein the handle is sufficiently flexible for an operator to squeeze the first and second elongated delivery devices together.

20. A method for implanting a sling under a urethra in a body of a patient, the method comprising:
    threading an end of a sleeve at least partially enclosing a sling through an aperture near a distal end of a delivery device, through a lumen extending along at least a portion of a length of the delivery device, and out an aperture near a proximal end of the delivery device;
    inserting the distal end of the delivery device through an incision in a vaginal wall to a first side of the urethra;
    sliding the sleeve off the sling through the lumen of the delivery device out of the body of the patient; and
    leaving the sling in the body of the patient to support the urethra.

21. The method of claim 20 comprising positioning an end of the sling in front of the pubic bone.

22. The method of claim 20 comprising positioning an end of the sling behind the pubic bone.

23. The method of claim 20 comprising positioning an end of the sling near the pubic bone.

24. The method of claim 20 comprising positioning an end of the sling near an obturator foramen.

25. The method of claim 20 comprising positioning an end of the sling through an obturator foramen.

26. The method of claim 20 comprising, making no incisions other than to the vaginal wall.

* * * * *